United States Patent
Neumann

(10) Patent No.: US 8,879,898 B2
(45) Date of Patent: Nov. 4, 2014

(54) VOLATILE MATERIAL DISPENSING SYSTEM

(75) Inventor: Hermann Neumann, Kenosha, WI (US)

(73) Assignee: S.C. Johnson & Son, Inc., Racine, WA (US)

( * ) Notice: Subject to any disclaimer, the term of this patent is extended or adjusted under 35 U.S.C. 154(b) by 269 days.

(21) Appl. No.: 13/438,721

(22) Filed: Apr. 3, 2012

(65) Prior Publication Data

US 2012/0199665 A1    Aug. 9, 2012

Related U.S. Application Data

(63) Continuation of application No. 12/313,999, filed on Nov. 26, 2008, now abandoned.

(60) Provisional application No. 61/004,401, filed on Nov. 26, 2007.

(51) Int. Cl.
| | | |
|---|---|---|
| *A61M 16/00* | (2006.01) | |
| *A61L 9/03* | (2006.01) | |
| *A01M 1/20* | (2006.01) | |

(52) U.S. Cl.
CPC ............... *A61L 9/03* (2013.01); *A01M 1/2077* (2013.01); *A61L 2209/12* (2013.01)
USPC ............ 392/392; 392/386; 392/393; 219/541

(58) Field of Classification Search
None
See application file for complete search history.

(56) References Cited

U.S. PATENT DOCUMENTS

| | | |
|---|---|---|
| 2,942,090 A | 6/1960 | Diehl |
| 3,581,266 A | 5/1971 | Weyenberg |
| 4,037,082 A | 7/1977 | Tamada et al. |
| 4,549,250 A | 10/1985 | Spector |
| 4,629,604 A | 12/1986 | Spector |
| 4,714,984 A | 12/1987 | Spector |
| 4,785,642 A | 11/1988 | Chin et al. |
| 4,804,821 A | 2/1989 | Glucksman |
| 4,849,606 A | 7/1989 | Martens, III et al. |
| 4,853,517 A | 8/1989 | Bowen |
| 5,014,913 A | 5/1991 | Hoyt et al. |
| 5,111,477 A | 5/1992 | Muderlak |
| 5,136,684 A | 8/1992 | Lonker et al. |
| 5,175,791 A | 12/1992 | Muderlak et al. |
| 5,213,523 A | 5/1993 | Hygema et al. |
| 5,402,517 A | 3/1995 | Gillett et al. |
| 5,521,357 A | 5/1996 | Lock et al. |

(Continued)

FOREIGN PATENT DOCUMENTS

| | | |
|---|---|---|
| EP | 1283062 | 2/2003 |
| FR | 1596401 | 6/1970 |

(Continued)

OTHER PUBLICATIONS

International Search Report and Written Opinion dated Aug. 10, 2007, Appl. No. PCT/US2007/008119.

(Continued)

*Primary Examiner* — Thor Campbell

(57) ABSTRACT

A modular volatile material dispensing system includes a supporting plate having a front side and a rear side. The rear side of the supporting plate is configured to removably attach to an electrical plate and a non-electrical plate. The modular volatile material dispensing system includes a cover plate attached to the front side of the supporting plate to form a compartment therebetween, which is adapted to hold a volatile material therein.

6 Claims, 23 Drawing Sheets

(56) References Cited

U.S. PATENT DOCUMENTS

| | | |
|---|---|---|
| 5,556,192 A | 9/1996 | Wang |
| 5,574,821 A | 11/1996 | Babasade |
| 5,577,156 A | 11/1996 | Costello |
| 5,647,052 A | 7/1997 | Patel |
| 5,735,460 A | 4/1998 | Eisenbraun |
| 5,788,155 A | 8/1998 | Martin et al. |
| 5,845,847 A | 12/1998 | Martin et al. |
| 5,882,256 A | 3/1999 | Shropshire |
| 5,937,140 A | 8/1999 | Leonard et al. |
| 5,945,094 A | 8/1999 | Martin et al. |
| 5,976,503 A | 11/1999 | Martin et al. |
| 6,072,165 A | 6/2000 | Feldman |
| 6,085,026 A | 7/2000 | Hammons et al. |
| 6,097,881 A | 8/2000 | DeWitt et al. |
| 6,104,866 A | 8/2000 | DeWitt |
| 6,123,935 A | 9/2000 | Wefler et al. |
| 6,141,496 A | 10/2000 | Sundberg et al. |
| 6,289,176 B1 | 9/2001 | Martter et al. |
| 6,293,474 B1 | 9/2001 | Helf et al. |
| 6,296,196 B1 | 10/2001 | Denen et al. |
| 6,341,732 B1 | 1/2002 | Martin et al. |
| 6,378,780 B1 | 4/2002 | Martens, III et al. |
| 6,382,522 B2 | 5/2002 | Tomkins et al. |
| 6,386,462 B1 | 5/2002 | Martens, III |
| 6,439,474 B2 | 8/2002 | Denen |
| 6,446,880 B1 | 9/2002 | Schram et al. |
| 6,450,419 B1 | 9/2002 | Martens, III et al. |
| D463,736 S | 10/2002 | Hern |
| D463,737 S | 10/2002 | Hern |
| D464,416 S | 10/2002 | von Dohlen et al. |
| 6,478,440 B1 | 11/2002 | Jaworski et al. |
| 6,482,863 B2 | 11/2002 | Munagavalasa et al. |
| D471,087 S | 3/2003 | McCoy et al. |
| 6,569,387 B1 | 5/2003 | Furner et al. |
| RE38,150 E | 6/2003 | Greatbatch et al. |
| 6,706,988 B1 | 3/2004 | Helf et al. |
| 6,714,725 B2 | 3/2004 | Grone et al. |
| 6,752,327 B2 | 6/2004 | Martens, III et al. |
| 6,768,865 B2 | 7/2004 | Stathakis et al. |
| 6,786,427 B2 | 9/2004 | Schram et al. |
| 6,789,741 B2 | 9/2004 | Varanasi et al. |
| 6,790,408 B2 | 9/2004 | Whitby et al. |
| 6,793,149 B2 | 9/2004 | Schramm et al. |
| 6,810,204 B2 | 10/2004 | Grone et al. |
| 6,843,430 B2 | 1/2005 | Boticki et al. |
| 6,853,801 B2 | 2/2005 | Wefler |
| 6,857,580 B2 | 2/2005 | Walter et al. |
| 6,859,615 B2 | 2/2005 | Yip et al. |
| 6,894,193 B2 | 5/2005 | Zehner et al. |
| 6,917,754 B2 | 7/2005 | Pedrotti et al. |
| 6,957,012 B2 | 10/2005 | He et al. |
| 6,969,008 B2 | 11/2005 | Helf et al. |
| 6,996,335 B2 | 2/2006 | Zobele |
| 7,017,829 B2 | 3/2006 | Martens, III et al. |
| 7,046,919 B2 | 5/2006 | Shimizu et al. |
| 7,070,121 B2 | 7/2006 | Schramm et al. |
| 7,088,914 B2 | 8/2006 | Whittle et al. |
| D532,093 S | 11/2006 | Helf et al. |
| D534,640 S | 1/2007 | Helf et al. |
| 7,252,244 B2 | 8/2007 | Martens, III |
| 7,277,626 B2 | 10/2007 | Pesu et al. |
| 7,344,123 B2 | 3/2008 | Pankhurst et al. |
| 7,389,943 B2 | 6/2008 | Jaworski |
| 2002/0023639 A1 | 2/2002 | Flierl et al. |
| 2004/0033171 A1 | 2/2004 | Kvietok et al. |
| 2004/0124988 A1 | 7/2004 | Leonard et al. |
| 2004/0247300 A1 | 12/2004 | He |
| 2005/0285538 A1 | 12/2005 | Jaworski |
| 2006/0000920 A1 | 1/2006 | Leonard |
| 2006/0118583 A1 | 6/2006 | Christianson |
| 2006/0237439 A1 | 10/2006 | Norwood |
| 2007/0075159 A1 | 4/2007 | Lin |
| 2007/0248502 A1 | 10/2007 | Adair et al. |
| 2008/0023568 A1 | 1/2008 | Weggelaar |
| 2008/0169355 A1 | 7/2008 | Pohl et al. |
| 2009/0134239 A1 | 5/2009 | Neumann |

FOREIGN PATENT DOCUMENTS

| | | |
|---|---|---|
| GB | 2117639 | 10/1983 |
| GB | 2228681 | 5/1990 |
| GB | 2275609 | 7/1994 |
| GB | 2401548 | 11/2004 |
| JP | 06-320083 | 11/1994 |
| JP | 10263068 A | 10/1998 |
| WO | WO02/020172 | 3/2002 |
| WO | WO03/070287 | 8/2003 |
| WO | WO2004/020002 A2 | 3/2004 |
| WO | WO2007/048178 | 3/2007 |

OTHER PUBLICATIONS

International Search Report and Written Opinion dated Mar. 16, 2009, Appl. No. PCT/US2008/013169.

US 8,879,898 B2

VOLATILE MATERIAL DISPENSING SYSTEM

CROSS REFERENCE TO RELATED APPLICATIONS

This application is a continuation of U.S. patent application Ser. No. 12/313,999, filed on Nov. 26, 2008, which claims the benefit of U.S. Provisional Application Ser. No. 61/004,401, filed Nov. 26, 2007, and each application is incorporated herein by reference in its entirety.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure relates generally to a volatile material dispensing system and, more specifically, to a volatile material dispensing system capable of multiple operating states.

2. Description of the Background of the Invention

Typical volatile material dispensers provide for either the passive or active emission of volatiles into the atmosphere. For example, one typical prior art system discloses a container having a reservoir filled with a fragrance laden gel. The reservoir includes an open end and a peripheral flange extending therearound. A vapor permeable membrane is secured to the peripheral flange over the open end and an impermeable membrane is removably secured to the permeable membrane. The container is releasably inserted into an electrically heated vapor apparatus. During use, an electrical plug extending from the body is inserted into a conventional wall outlet. Heat from a heating element assists in the volatilization of the fragrance, which is thereafter diffused through the permeable membrane and slots within the body.

In a different prior art system, a warming apparatus includes a housing that has a heating surface. A heating element located within the housing is adapted to provide heat to the heating surface. The housing further includes a lighting means, typically in the form of LED's, which is adapted to illuminate an object located on the heating surface. An adjustable cord provides electricity to the housing. A switch provides a way to activate and deactivate the heating surface and/or the light source.

The present disclosure contemplates various volatile material dispensing systems that provide for more effective diffusion of volatiles into the atmosphere. In one embodiment, a user may operate the dispensing system to either actively or passively diffuse a volatile material depending on the user's preference. By providing for both active and passive volatile diffusion in one dispensing system, the user may adjust the rate of volatile diffusion and/or conserve energy. All of the embodiments disclosed herein further utilize convenient frames and/or other structures to allow for easy conversion from an active to passive system or vice versa.

SUMMARY OF THE INVENTION

According to one aspect of the present invention, a modular volatile material dispensing system includes a supporting plate having a front side and a rear side. The rear side of the supporting plate is configured to removably attach to an electrical plate and a non-electrical plate. The modular volatile material dispensing system includes a cover plate attached to the front side of the supporting plate to form a compartment therebetween, which is adapted to hold a volatile material therein.

In a different aspect of the present invention, a modular volatile material dispensing system includes a supporting plate having a front side and a rear side and an opening extending therethrough. The rear side of the supporting plate is configured to removably attach to an electrical plate including a heating element and electrical prongs, and a non-electrical plate including an adapter selected from the group consisting of a substantially U-shaped clip adapter having first and second arms, a substantially L-shaped support adapter, a hook adapter, and a clip adapter. The modular volatile material dispensing system also includes a cover plate releasably attached to the front side of the supporting plate to form a compartment therebetween, and a volatile material dispenser adapted to be held within the compartment.

In yet another aspect of the present invention, a modular volatile material dispensing system includes a supporting plate having a front side and a rear side. The supporting plate is configured to attach to at least one of an electrical plate and a non-electrical plate. The modular volatile material dispensing system also includes a cover plate releasably attached to the front side of the supporting plate to selectively form a compartment therebetween. The cover plate is removable from the support plate to allow access to the compartment. The modular volatile material dispensing system further includes a volatile material dispenser having a reservoir with a permeable membrane disposed within the compartment.

BRIEF DESCRIPTION OF THE DRAWINGS

Other aspects and advantages of the present invention will become apparent upon consideration of the following detailed description, wherein similar structures have similar reference numerals.

DETAILED DESCRIPTION

Figure 1:
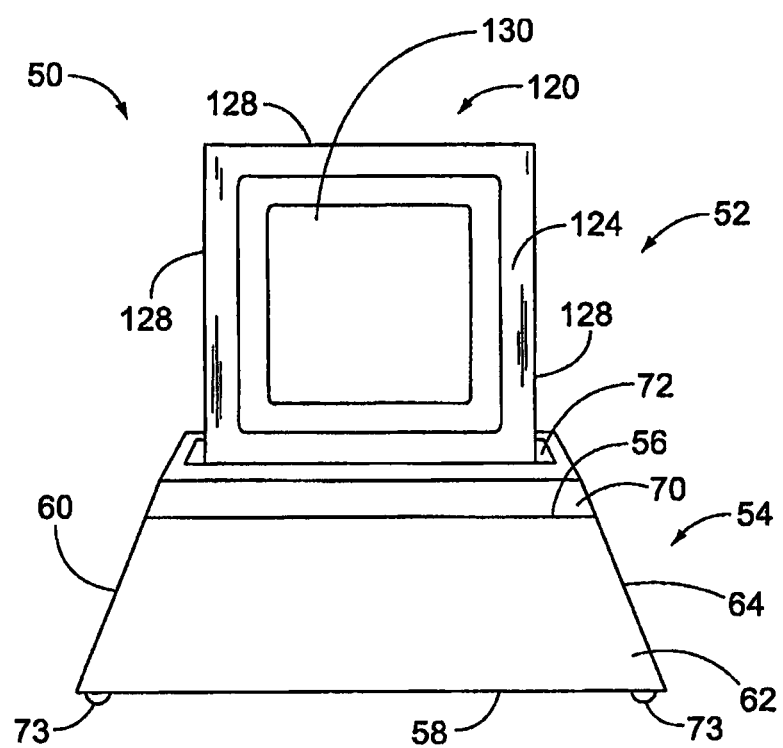
FIG. 1 is a front elevational view of a first embodiment of a volatile material dispensing system showing a support device and a dispensing device.
Figure 2:
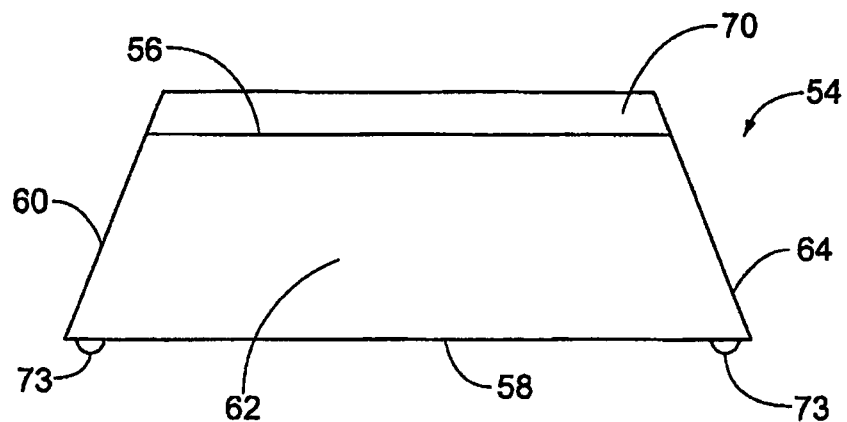
FIG. 2 is a front elevational view of the support device of FIG. 1.
Figure 3:
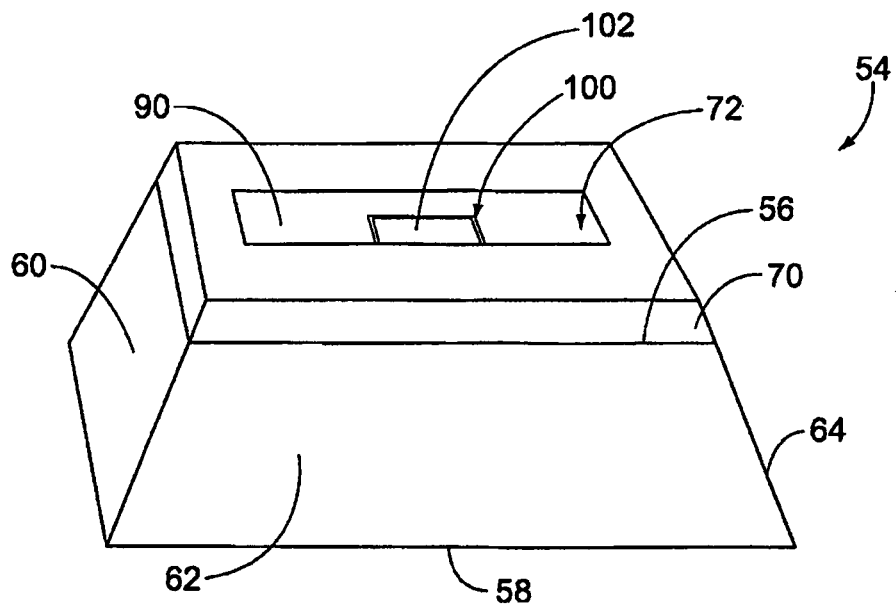
FIG. 3 is a front isometric view of the support device of FIG. 1.
Figure 4:
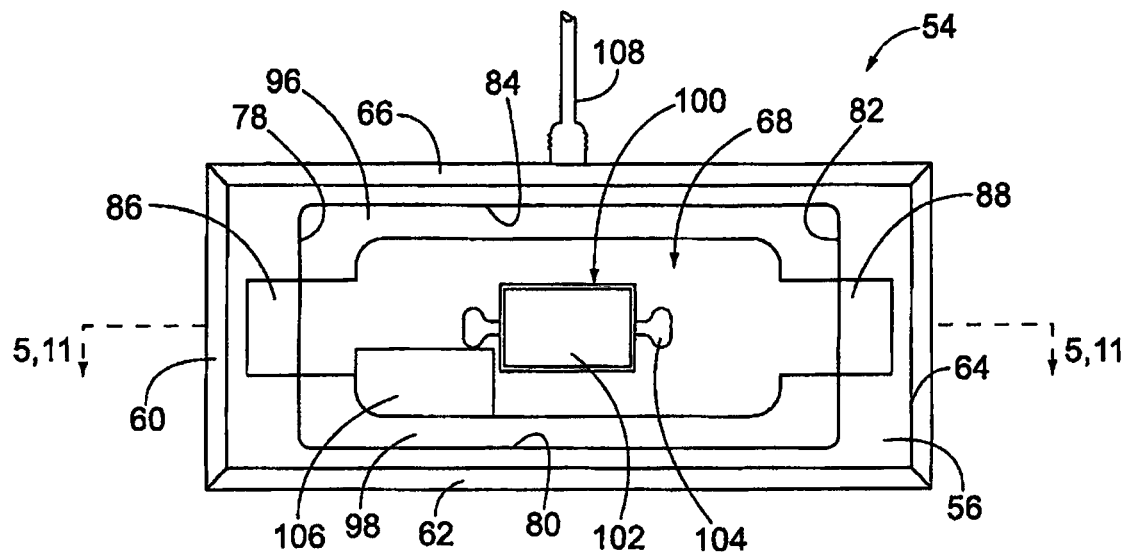
FIG. 4 is a top plan view of the support device of FIG. 1 with a cover removed to show portions of an interior of the support device.

Referring to FIG. 1, a volatile material dispensing system 50 generally includes a dispensing device 52 and a support base 54. FIGS. 2-4 depict the support base 54 as comprising a generally trapezoid shape having a top end 56, a bottom end 58, and four sidewalls 60, 62, 64, 66. The base sidewalls 60-66 extend upwardly and inwardly from the bottom end 58 toward the top end 56. The bottom end 58 of the support base 54 is preferably about 2 inches wide by about 5 inches long. The top end 56 of the support base 54 is preferably about 1.8 inches wide by about 3.5 inches long. An orifice 68 is provided within the top end 56 of the support base 54. A trapezoidal cover 70 overlies the top end 56 of the support base 54.

As seen in FIGS. 1-3, a rectangular opening 72 is provided within the cover 70. The rectangular opening 72 is aligned with the larger orifice 68 within the support base 54. The cover 70 is provided to obstruct the visibility of interior portions of the support base 54, e.g., to hide internal wiring and circuitry (not shown). The support base 54 is preferably made of a polymer material such as polypropylene, but can also be made of any other suitable material. The cover 70 is preferably made of a similar material as that of the support base 54. The cover 70 is secured to the support base 54 by a snap-fit or other mechanical connection. In other embodiments, the cover 70 is formed integrally with the top end 56 of the support base 54.

With reference to FIGS. 2 and 3, it will be apparent to one skilled in the art that the support base 54 may be designed to comprise other shapes than the present trapezoidal configuration. For example, the support base 54 may comprise a square, a rectangle, or any other geometric shape that can provide adequate support for the volatile material dispensing system 50. The support base 54 also includes legs 73 (see FIGS. 1 and 2) to provide additional support to the volatile material dispensing system 50 and raise the support base 54 off of a surface (not shown).

Figure 5:
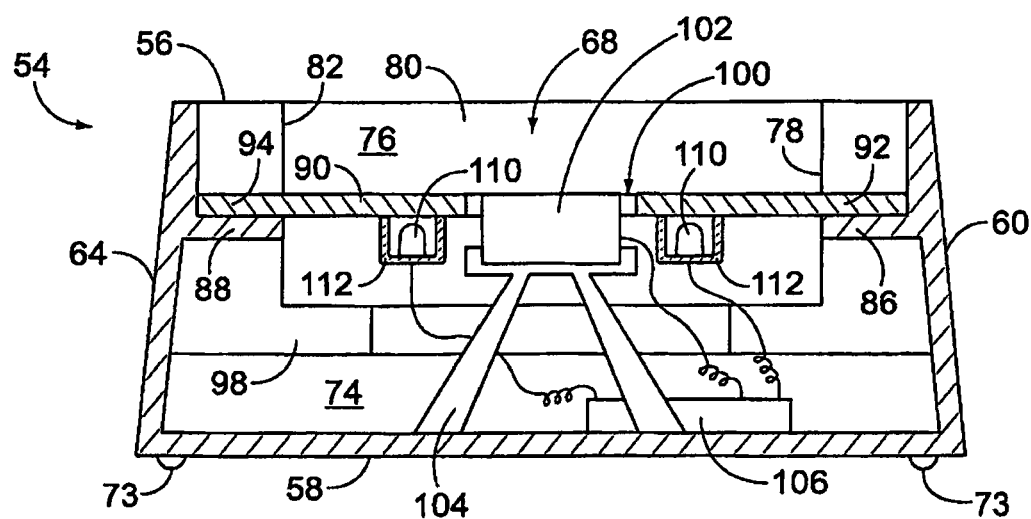
FIG. 5 is a partial sectional view of the support device of FIG. 1 taken generally along the line 5-5 of FIG. 4.

Turning to FIG. 3, it can be seen that the rectangular opening 72 is centered over the top end 56 of the support base 54. FIGS. 4 and 5 depict the support base 54 with the cover 70 removed from the top end 56 to expose the orifice 68, which is similarly centrally disposed within the top end 56 of the support base 54. The orifice 68 includes a lower chamber 74 and an upper chamber 76 (see FIG. 5). The upper chamber 76 comprises four walls 78, 80, 82, 84 provided in a generally rectangular configuration (see FIG. 4). Two ledges 86, 88 (see FIGS. 4 and 5) are disposed in opposing walls 78 and 82, respectively, and are substantially rectangular in shape. The lower chamber 74 is depicted as having a generally race-track shaped opening that provides access to internal portions of the support base 54, which will be described in further detail below. It is also contemplated that the orifice 68 and the rectangular opening 72 may comprise other shapes in keeping with the disclosure provided herein.

As shown in FIGS. 3-5, a platform 90 extends across portions of the upper chamber 76. Turning to FIG. 5, it is shown that the platform 90 includes opposing protruding ends 92, 94 that rest on portions of the ledges 86, 86, respectively. FIG. 5 further depicts the platform 90 extending across the orifice 68 between the sidewalls 78 and 82. In other embodiments, the platform 90 may or may not extend across the entirety of the orifice 68 or may rest upon other internal supporting surfaces such as side ledges 96, 98. The platform 90 is preferably made of a transparent polymeric material such as polypropylene. The protruding ends 92, 94 of the platform 90 are preferably attached to the ledges 86, 88 using screws (not shown). In other embodiments, the protruding ends 92, 94 of the platform are attached to the ledges 86, 88 by an adhesive or other mechanical fastener to prevent removal of the platform 90 from the support base 54. The platform 90 may also be integrally formed as part of the support base 54. The platform 90 further includes a centrally disposed recess or opening 100, which is adapted to receive a heating element 102.

Referring again to FIGS. 3-5, the heating element 102 preferably extends upwardly through the opening 100 in the platform 90 so that a top end of the heating element 102 is flush with the platform 90. Although the heating element 102 is depicted as being centrally disposed within the orifice 68 and the platform 90, the heating element 102 may be off-centered in one or more of the orifice 68 and the platform 90. Further, the heating element 102 and/or the opening 100 may span the entire platform 90, a portion of the platform 90, or extend into the sidewalls 78-84. Additionally, the platform 90 may extend the entirety or a portion of the orifice 68 without the opening 100. If the platform 90 does not contain an opening 100, the heating element 102 is preferably disposed adjacent and possibly contacting the platform 90 from therebelow so that heat is conducted upwardly through the platform 90. The heating element 102 is preferably a ceramic covered resistor (as seen in FIGS. 4 and 5), but may also be any other type of heating element that controls heating as known to those of skill in the art.

As depicted in FIG. 5, the heating element 102 is preferably secured to the support base 54 by a brace 104. The brace 104 may be any size and shape so long as it holds the heating element 102 in the desired position. The heating element 102 is electrically connected to a circuit 106 located in the lower chamber 74 beneath the platform 90. The circuit 106 is preferably adapted to be used with the heating element 102. The circuit 106 may also be located elsewhere within the support base 54. The circuit 106 is connected to a power source via a cord 108 (see FIG. 4). The heating element 102 and the associated circuit 106 may be of any kind that is well known in the art such as the types described in U.S. Pat. Nos. 5,937,140, 6,478,440, 7,206,505, 7,288,748, and U.S. Patent Publication No. 2007/0237498, which are herein incorporated by reference in their entirety.

As shown in FIGS. 4 and 5, the platform 90 may optionally include a light source 110. The light source 110 is preferably at least one LED or another similarly adapted lighting element. The light source 110 may be embedded within the platform 90 as depicted in FIG. 5, located on the surface of the platform 90, or disposed beneath the surface of the platform 90 in the lower chamber 74. If the light source 110 is located beneath the surface of the platform 90, the platform 90 should preferably be made from a transparent material that allows light to pass through to an upper surface of the platform 90. Alternatively, the light source 100 may be located within the walls 78-84 defining the orifice 68. The light source 110 is depicted in FIG. 5 connected to the circuit 106, but the light source may be connected to an independent circuit (not shown). The light source 110 is preferably held in position and supported beneath the platform 90 using a holding member 112. The holding member 112 may take any form so long as it retains the light source 110 in the desired position. The light source 110 may include a variety of colors and configurations that are adapted to display a light show similar to the ones disclosed in U.S. Pat. Nos. 7,246,919, 7,375,476, and 7,419,281 and U.S. Patent Publication Nos. 2006/0158138, 2006/0176693, and 2007/0109782, which are herein incorporated by reference in their entirety.

The cord 108 depicted in FIG. 4 extends from the support base 54 and is adapted to be plugged into an electrical outlet (not shown). It is also contemplated that other power sources and electrical connections may be used as known to those of skill in the art. When the cord 108 is plugged into an electrical outlet (not shown), electrical power is supplied to the circuit 106. The circuit 106 in turn supplies power to the heating element 102 and/or the light source 110. The activation may occur when the cord 108 is plugged in, when a switch (not shown) is placed in an on position, and/or in response to a sensor, which will be discussed in more detail below.

Figure 6:
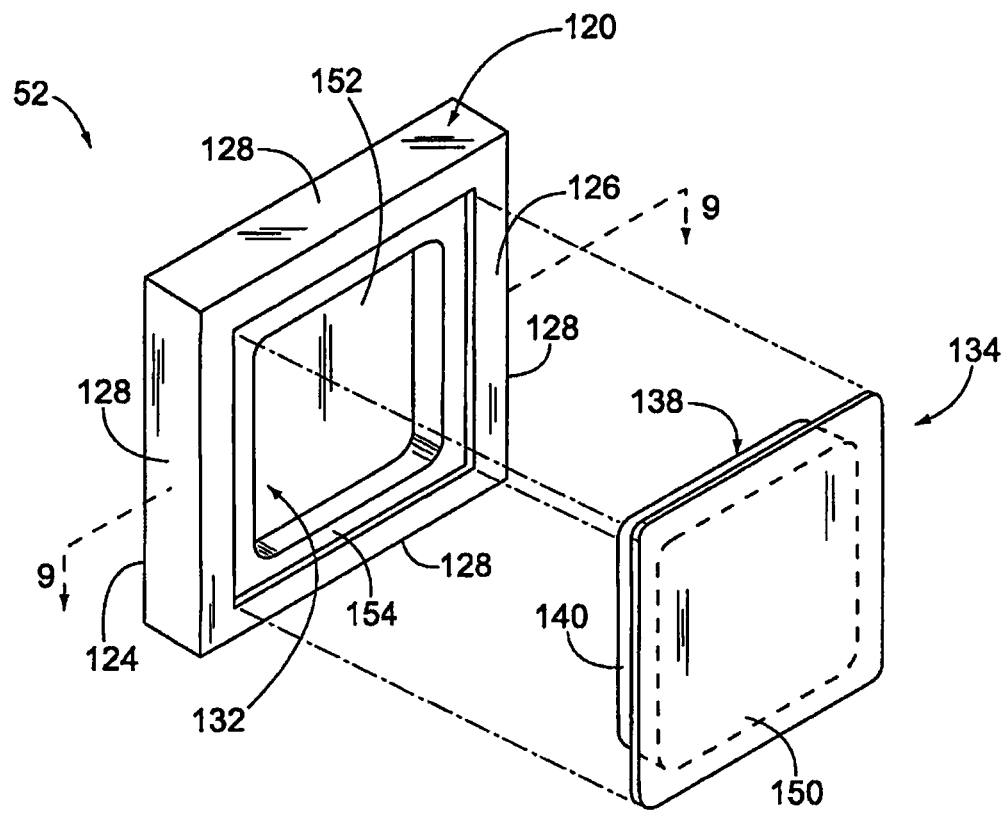
FIG. 6 is a front exploded isometric view of the dispensing device of FIG. 1 showing a frame and a material dispenser.
Figure 7:
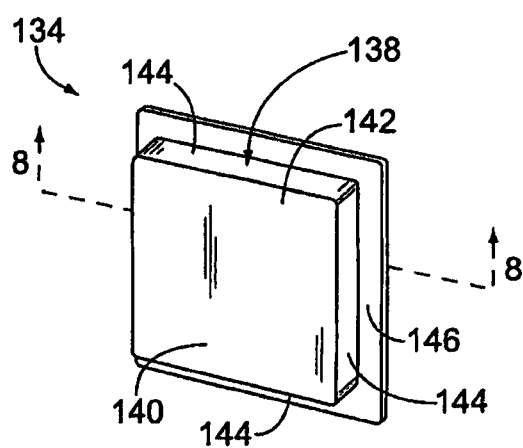
FIG. 7 is a rear isometric view of the material dispenser of FIG. 6.

Turning now to FIGS. 6 and 7, the dispensing device 52 is illustrated. The dispensing device 52 includes a frame 120 having a front face 124, a rear face 126, and four sidewalls 128. The four sidewalls 128 are preferably the same length and width and are planar and perpendicularly disposed in relation to the front face 124 and the rear face 126. Additionally, while the frame 120 is depicted as having a square shape, the frame 120 may be designed to comprise any number of shapes including, but not limited to, rectangular, oval, or pyramidal shapes. The frame 120 may be constructed from a variety of compositions, including glass, injection-molded plastic, or copolyester resin. In the preferred embodiment, the frame 120 is constructed from molded glass that is clear and transparent.

The front face 124 and the rear face 126 include a front recess 130 and a rear recess 132, respectively. As seen in FIG. 6, the rear recess 132 is adapted to receive an evacuatable material dispenser 134 that contains a volatile material 136 (see FIG. 8). Frame 120 preferably has a thickness of between about 12 mm and about 22 mm and a height and width of between about 70 mm and about 90 mm. More preferably, frame 120 has a width of approximately 15 mm and height of approximately 80 mm. The frame 120 also preferably has a surface area greater than about 3000 mm$^2$. The frame 120 is similar to the frames described in U.S. Pat. No. 7,213,770, which is herein incorporated by reference in its entirety.

Figure 8:
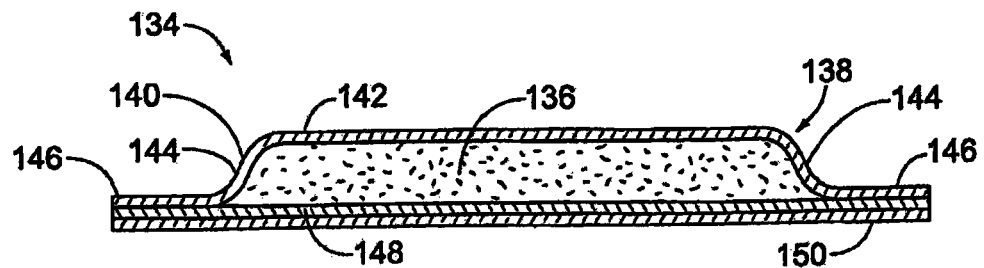
FIG. 8 is a sectional view taken generally along the line 8-8 of FIG. 7 showing the material dispenser in a full state.
Figure 9:
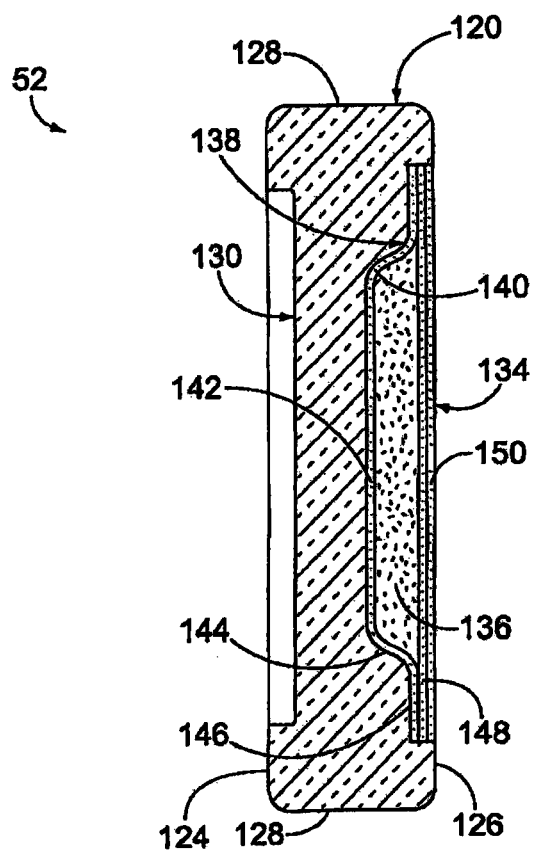
FIG. 9 is a sectional view taken generally along the line 9-9 of FIG. 6 showing the material dispenser of FIG. 6 in a full state and within a recess of the frame.

Now turning to FIGS. 7 and 8, the material dispenser 134 includes a blister 138 comprising a cup-shaped structure 140 that includes a bottom wall 142 and sidewalls 144 that extend therefrom and terminate at a surrounding flange 146. A non-porous permeable membrane 148 is adhered to the surrounding flange 146 and extends across the cup-shaped structure 140. The permeable membrane 148, in conjunction with the bottom wall 142 and the sidewalls 144, acts as a sealed reservoir to contain the volatile material 136. An impermeable laminate 150 is releasably adhered to the blister 138 over the permeable membrane 148. The material dispenser 134 is similar to the material dispensers described in U.S. Pat. No. 7,441,360, which is herein incorporated by reference in its entirety.

Referring again to FIG. 6, the rear recess 132 is configured to receive the material dispenser 134. Specifically, the bottom wall 142 of the cup-shaped structure 140 is disposed within an inner recess 152 of the rear recess 132. Further, the surrounding flange 146 is disposed within a peripheral recess 154 of the rear recess 132. The rear recess 132 is preferably shaped in a complementary fashion to that of the cup-shaped structure 140 so that same may be nested within the rear recess 132 while the permeable membrane 148 and the impermeable laminate 150 are exposed to the ambient environment, i.e., away from the rear face 126 of the frame 120. The material dispenser 134 of the present embodiment is permanently attached to the frame 120. However, in other embodiments the material dispenser 134 is adapted to be releasably attached to the frame 120. In any of the embodiments, the material dispenser 134 may be attached to the rear face 126 of the frame 120 by an adhesive, a friction fit between portions of the material dispenser 134 and the portions of the frame 120 defining the rear recess 132, or by any other securement mechanism known to those of skill in the art. In yet another embodiment, it is contemplated that the material dispenser 134 may be held within the frame 120 by the sidewalls 60-66 of the support base 54.

As noted above, the blister 138 of the material dispenser 134 is filled with the volatile material 136. The volatile material 136 may comprise an active ingredient for diffusion into the surrounding atmosphere, such as a fragrance, air freshener, odor eliminator, or insect repellant insecticide. It is contemplated that any type of volatile material suited for dispersal through a permeable membrane may be used with the present embodiments described herein.

During a non-use state of the material dispenser 134, the impermeable laminate 150 prevents (or substantially prevents) diffusion of the volatile material 136 through the permeable membrane 148. During an in use state, the impermeable laminate 150 is removed from the blister 138. A user removes the impermeable laminate 150 by grasping an end thereof and peeling it off the blister 138. A tab, extension, or other means for grasping (not shown) may be included as an extension of the impermeable laminate 150 to aid in removal of same. The extension (not shown) is preferably provided at a corner of the impermeable laminate 150, but may extend from any portion thereof. Following removal of the impermeable laminate 150 the material dispenser 134 transitions from a full or first condition toward an empty or second condition, which allows for the volatile material 136 to be dispersed into the atmosphere.

Figure 10:
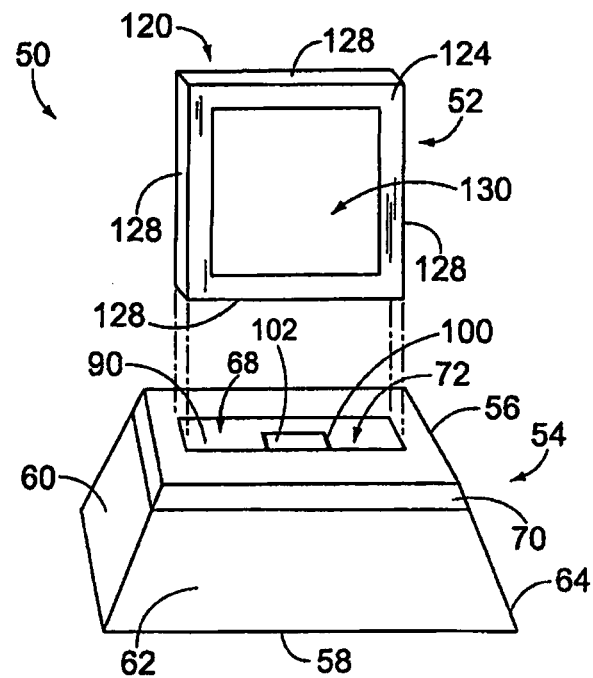
FIG. 10 is a front exploded isometric view of the volatile material dispensing system shown in FIG. 1.
Figure 11:
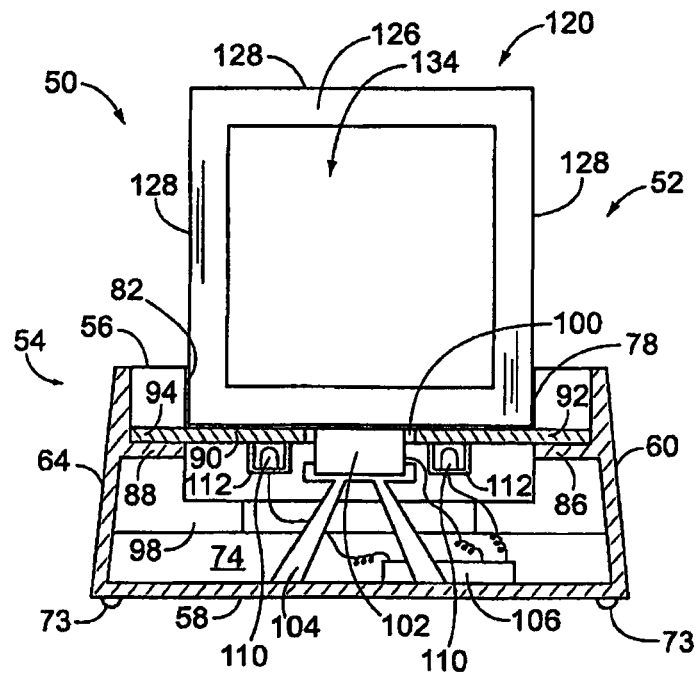
FIG. 11 is a partial sectional view taken generally along the line 11-11 of FIG. 4.

The volatile material dispensing system 50 of the present embodiment may operate in a passive or first operating state and an active or second operating state. In the first operating state, the dispensing device 52 is inserted into the support base 54 (see FIGS. 1 and 11). FIG. 10 shows how one of the sidewalls 128 of the dispensing device 52 is aligned with the rectangular opening 72 in the cover 70 of the support base 54. Upon insertion of the sidewall 128 into the opening 72, the sidewall 128 rests upon the platform 90 to provide support to the dispensing device 52 and to dispose the heating element 102 in thermal contact with the sidewall 128. The dispensing device 52 is stably held within the support frame 54 by one or more of the platform 90, portions of the frame 120 (front face 124, rear face 126, and sidewalls 128) that interact with interior portions of the ledges 86, 88 and the walls 78-84, and portions of the cover 70 that define the opening 72. Any of the preceding structure that assists in the support of the dispensing, device 52 may similarly act as a guide and/or orientation mechanism to ensure the effective alignment of the dispensing device 52 with the heating element 102 and the appropriate orientation of the dispensing device 52 within the support frame 54. Upon removal of the impermeable laminate 150 and insertion of the dispensing device 52 within the support frame 54, the volatile material dispensing system 50 is functioning in the first operating state to passively emit the volatile material 136 through the permeable membrane 148 and into the atmosphere.

The volatile material dispensing system 50 may be placed into the second operating state by activating the heating element 102. Activation of the heating element 102 causes thermal energy from the heating element 102 to be transferred through the sidewall 128 in thermal contact with the heating element 102 and/or through the platform 90 and into the sidewall 128 in thermal contact with the platform 90. The thermal energy is conducted throughout the glass frame 120 and to the blister 138, wherein the thermal energy assists in the volatilization of the volatile material 136 by increasing the rate of diffusion of same through the permeable membrane 148 and into the atmosphere. The increased diffusion rate allows for a stronger concentration of the volatile material 136 in a given area and/or the ability to effectively disperse the volatile material 136 to a larger area. The heating element 102 may be activated by plugging in the cord 108 of the support base 54, by placing a switch (not shown) in an on position that allows for immediate or timed activation of the heating element 102, or in response to a sensor (not shown), which is discussed in greater detail below.

It is also contemplated that a controlling mechanism (not shown) may be incorporated into the support base 54 to change the positioning of the frame 120 in relation to the heating element 102. For example, to create a greater rate of diffusion the user may want to position the frame 120 directly in contact with the heating element 102. Alternatively, the user could adjust the controlling mechanism to move the frame 120 a desired distance away from the heating element 102 to decrease the rate of diffusion.

Figure 12:
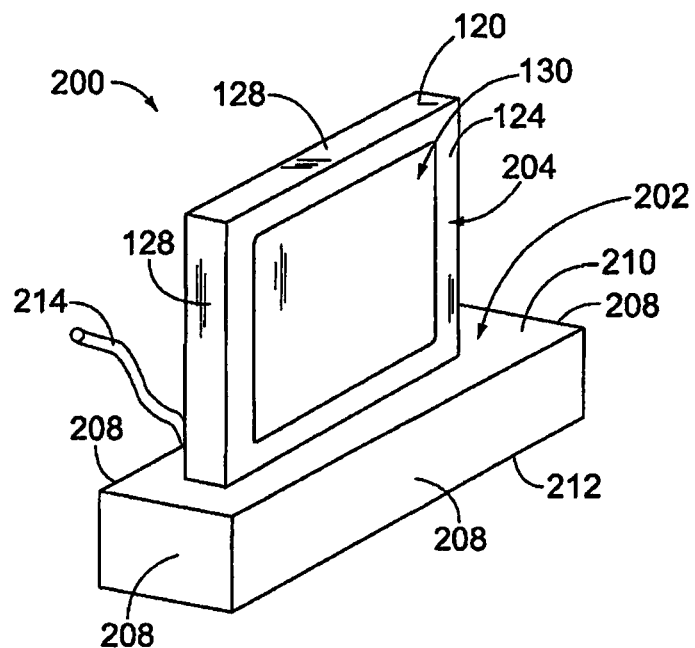
FIG. 12 is a front isometric view of an alternative embodiment of a volatile material dispensing system showing a base and a dispensing device.
Figure 13:
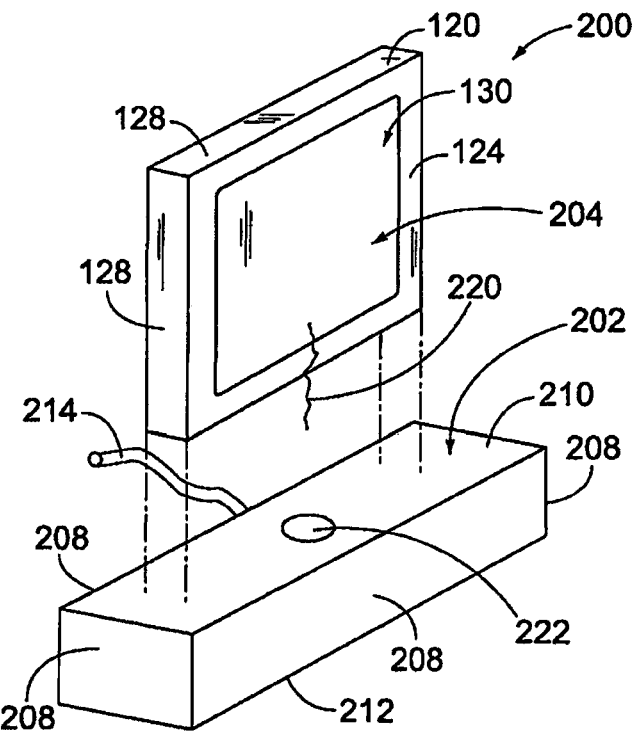
FIG. 13 is a front exploded isometric view of the volatile material dispensing system of FIG. 12.

FIGS. 12 and 13 depict an alternative embodiment of a volatile material dispensing system 200, which includes a base 202 and a dispensing device 204. The dispensing device 204 is identical to the dispensing device 52 described above except for the inclusion of additional structure described hereinbelow (like reference numerals are used for identical structure). Similar to the volatile material dispensing system 50 described above, the volatile material dispensing device 200 includes two distinct operating states, i.e., passive and active operating states. The passive or first operating state of the volatile material dispensing system 200 allows for the diffusion of the volatile material 136 in a similar manner as noted above in connection with the volatile material dispensing system 50. However, the active or second operating state of the volatile material dispensing system 200 includes a heating mechanism 206 (see FIGS. 14-15) for increasing the rate of volatile material diffusion.

As seen in FIGS. 12 and 13, the base 202 includes four sidewalls 208, a top wall 210, and a bottom wall 212. The base 202 comprises a substantially rectangular shape, which could take on any other geometric shape with regard to aesthetic and functional preferences. The base 202 contains circuitry (not shown) that is associated with operation of the volatile material dispensing device 200. A cord 214 extends from one of the sidewalls 208 of the base 202 and is adapted to be plugged into an electrical outlet (not shown). The base 202 may further include a switch (not shown) or some other manual or automatic activation means to operate the volatile material dispensing system 200. The frame 120 is secured to the top wall 210 of the base 202 using adhesive (not shown) or by some other securement means known to one of skill in the art.

Figure 14:
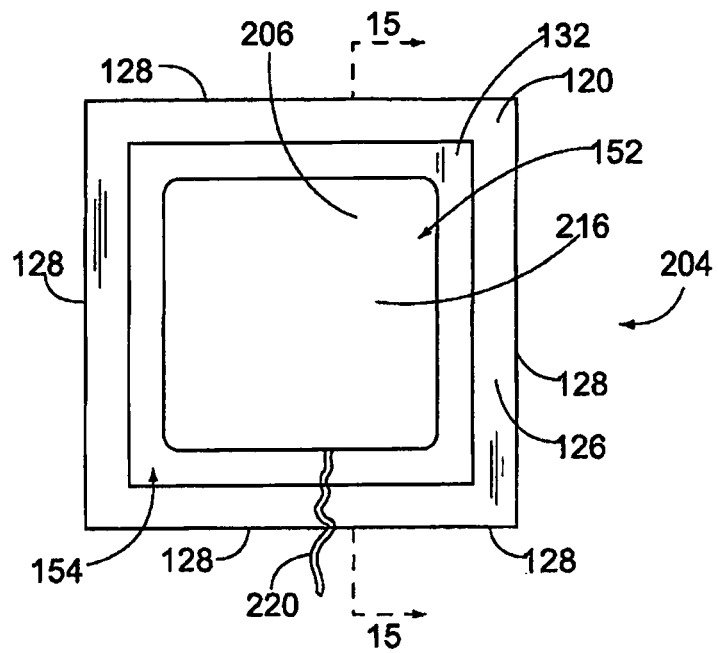
FIG. 14 is a front elevational view of the volatile material dispensing system of FIG. 12 without a material dispenser in a frame of the dispensing device.
Figure 15:
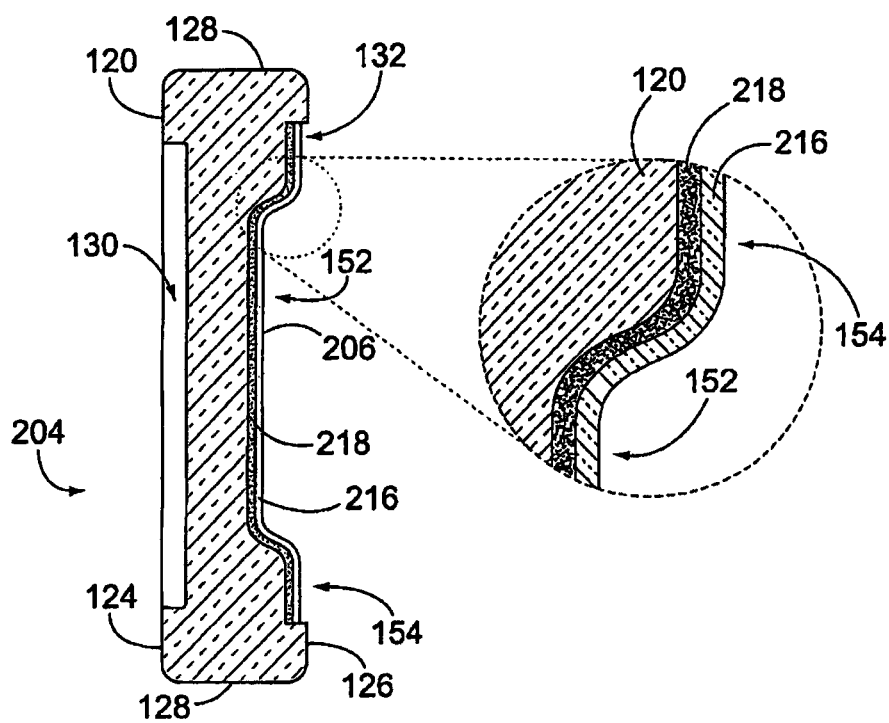
FIG. 15 is a sectional view taken generally along the line 15-15 of FIG. 14.

Turning to FIGS. 14 and 15, one particular embodiment of the heating mechanism 206 is shown. The heating mechanism 206 of the present embodiment comprises a film layer 216 that extends across a bottom wall defining the inner recess 152 of the rear recess 132. In different embodiments, the film layer 216 may extend across a portion of the inner recess 152 and/or the peripheral recess 154, all or part of the front recess 130, all or part of the front and rear faces 124, 126, or may be disposed within the frame 120 itself. The film layer 216 is secured to a wall defining the inner recess 152 by an adhesive 218 (see FIG. 15) or any other type of securing means. The film layer 216 is electrically connected to the base 202 by a wire 220 that extends from the film layer 216 toward one of the sidewalls 128. The wire 220 extends along an external portion of the frame 120 from the film layer 216 toward the sidewall 128 of the frame 120 disposed adjacent the top wall 210 of the base 202 to place the wire 220 in electrical communication with circuitry (not shown) disposed within the base 202. The base 202 preferably includes an opening 222 (see FIG. 13) to allow the wire 220 or other electrical connector in communication with the wire 220 to be electrically connected to the base 202. In other embodiments, the wire 220 extends through the frame 120 as opposed to extending across an external portion of the frame 120.

The film layer 216 preferably comprises a conductive polymer or a thin metal oxide. In the present embodiment, the film layer 216 comprises indium tin oxide, which is a transparent ceramic material that exhibits conductive properties. The film layer 216 may be applied by evaporation or sputtering vacuum coating to the glass frame 120. It is contemplated that other conductive materials known to those of skill in the art may similarly be used to form the film layer 216 and/or the wire 220. However, it is preferred that the film layer 216 and the wire 220 be transparent so they are not visible to a user. The heating mechanism 206 and associated film layer 216 may be of any kind that is well known in the art such as the type described in U.S. Pat. No. 7,039,304, which is herein incorporated by reference in its entirety.

Figure 16:
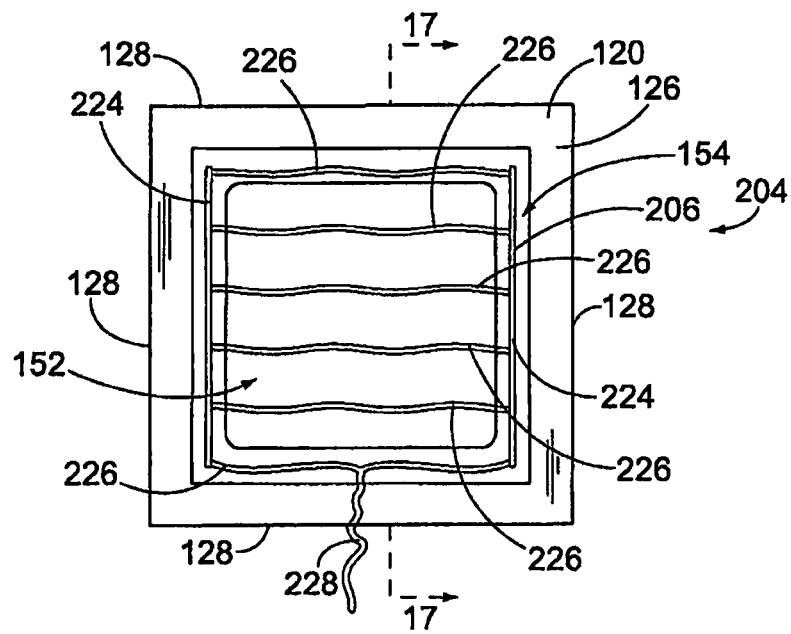
FIG. 16 is a front elevational view of a dispensing device similar to the one shown in FIG. 14 except that the present embodiment does not include a film layer.
Figure 17:
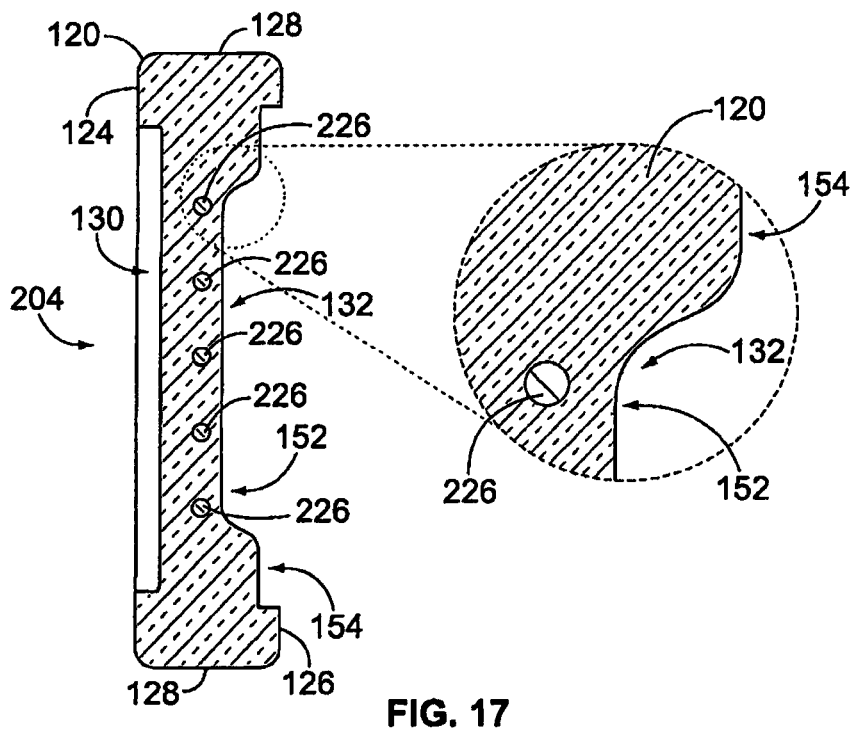
FIG. 17 is a sectional view taken generally along the line 17-17 of FIG. 16.

FIGS. 16 and 17 depict a second embodiment of the heating mechanism 206. The heating mechanism 206 of the present embodiment includes at least one electrode 224 disposed on or within the frame 120 (see FIG. 16), but may include two or more electrodes 224 to provide sufficient thermal energy to heat the frame 120 to a desired level. Preferably, the electrode(s) 224 cover a substantial length of the frame 120 and, more particularly, the length of the inner recess 152. The electrode(s) 224 may further include wires 226 that extend laterally on or throughout the frame 120. A connecting wire 228 electrically connects the electrode(s) 224 to a circuit (not shown) within the base 202. The electrode(s) 224, the wires 226, and the connecting wire 228 are preferably clear and/or transparent so they are not visible and may be constructed from any of the materials discussed herein. Alternatively, the wires 226 and electrode(s) 224 may be hidden from view by the design of the frame 120.

In the passive or first operating state, the cord 214 is unplugged or the base 202 is turned off by means of a switch (not shown), a sensor (not shown), or some other deactivation means. The volatile material dispensing system 200 acts in a similar manner as described above in connection with the volatile material dispensing system 50 in the passive operating state.

In the active or second operating state, the cord 214 is plugged into an electrical outlet to provide power to the heating mechanism 206. In some embodiments a switch (not shown), a sensor (not shown), or some other activation means may also be provided. In the active state, electrical energy is supplied to the heating mechanism 206 to cause thermal energy to be emanated through the film layer 216 or the electrode(s) 224. Thermal energy from the film layer 224 or the electrode(s) 224 passes through the glass frame 120 and to the blister 138 or directly to the blister 138 to assist in the volatilization of the volatile material 136 within the material dispenser 134 in a similar manner as noted above.

Figure 18:
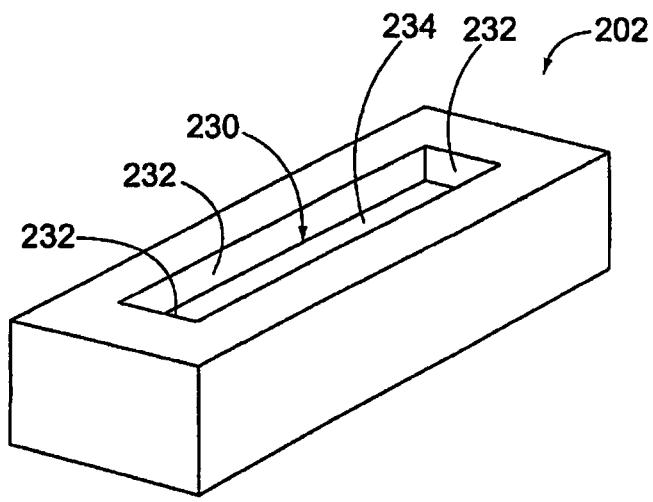
FIG. 18 is a front isometric view of a different embodiment of the base shown in FIGS. 12 and 13.

In an alternative embodiment, as shown in FIG. 18, the base 202 may have an orifice 230 for receipt of a portion of the frame 120 to assist in holding same in a stable manner. The orifice 230 is defined by a plurality of sidewalls 232 and a base wall 234. The frame 120 is inserted into the orifice 230 so that the frame 120 contacts the base wall 234 and the sidewalls 232 surround a portion of the frame 120. The orifice 230 is preferably shaped in a complementary way to the design of the frame 120 to further facilitate guiding the frame 120 into the base 202 and for stably supporting the frame 120. In the present embodiment, the wires 220, 228 extend through an opening (not shown) in the base wall 234 of the base 202.

FIGS. 19-23 depict yet another embodiment of a volatile material dispensing system 250, which is adapted to be easily converted from a stand alone device that dispenses a volatile material into the atmosphere to an electrically heated device that provides an increased rate of diffusion of a volatile material. The volatile material dispensing system 250 includes a housing 252, an electrical plate 254, and the material dispenser 134 described in connection with the other embodiments above (like reference numerals are used for identical structure). The housing 252 is generally donut-shaped and includes a front side 256, a back side 258, and a substantially flat bottom end 260. The bottom end 260 of the housing 252 is adapted to rest on a surface (not shown) and hold the housing 252 upright.

Figure 19:
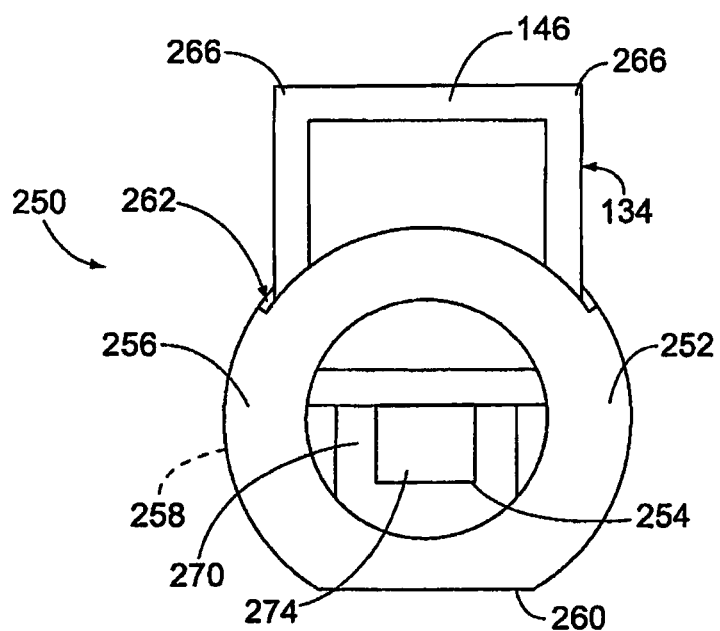
FIG. 19 is a front elevational view of another embodiment of a volatile material dispensing system that shows a material dispenser partially inserted into a housing.
Figure 21:
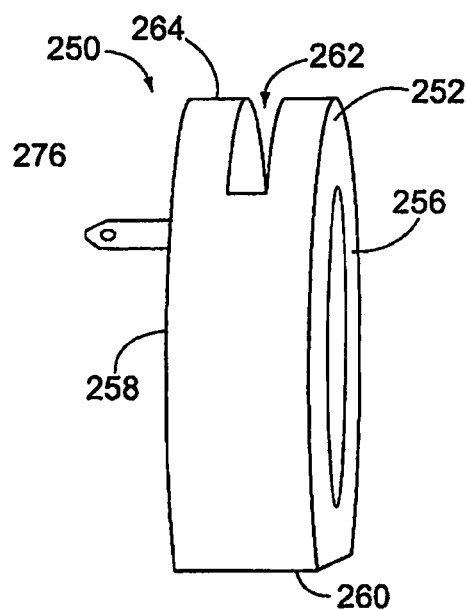
FIG. 21 is a side isometric view of the volatile material dispensing system of FIG. 19.
Figure 22:
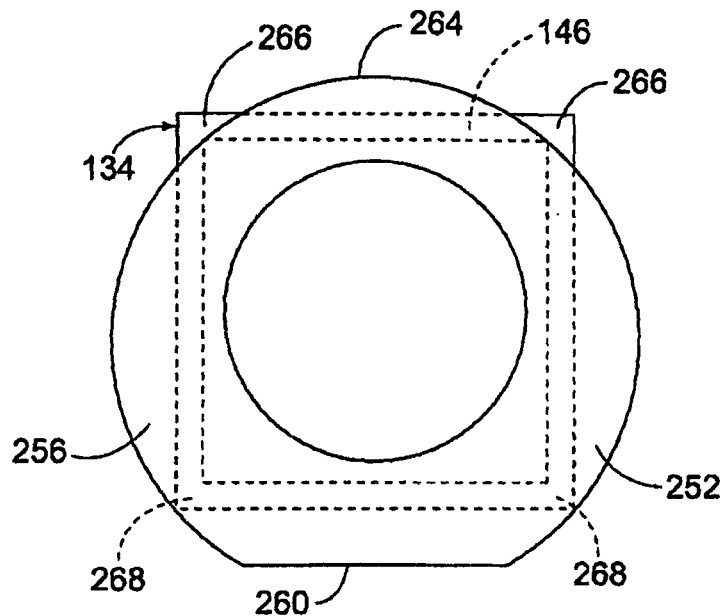
FIG. 22 is a front elevational view of the volatile material dispensing system shown in FIG. 19 with the material dispenser shown in dashed lines in a fully inserted position.
Figure 23:
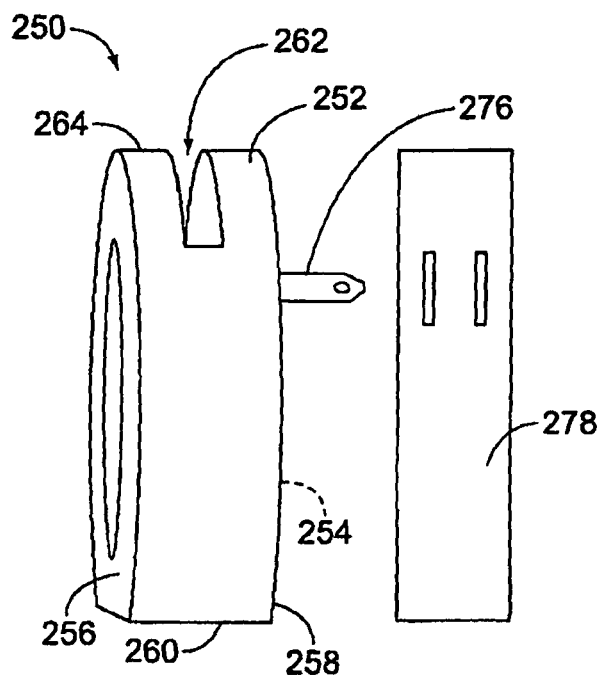
FIG. 23 is a view of the volatile material dispensing system similar to the one shown in FIG. 21 except that a different side of the volatile material dispensing system is shown and a schematic representation of an outlet is provided.

As shown in FIGS. 19, 21, and 23, the housing 252 further includes a slot 262 disposed within a top end 264 of the housing 252. The slot 262 is centered within the top end 264 and is generally rectangular in shape. The slot 262 has a width of about 1 mm, a length of about 8 mm, and a height that is preferably the length of the housing 252. Specifically, the slot 262 is sized to receive the material dispenser 134 almost substantially fully therein with only upper corners 266 of the surrounding flange 146 extending outwardly from the slot 262 (see FIG. 22). The slot 262 is preferably located opposite the bottom end 260 of the housing 252 to allow a user to insert the material dispenser 134 while the volatile material dispensing device 250 is in an upright position. When a user inserts the material dispenser 134 into the slot 262 the surrounding flange 146 interacts with walls defining the slot 262 to guide the material dispenser 134 therein and hold the material dispenser 134 in a stable position. Upon complete insertion of the material dispenser 134 into the slot 262, lower corners 268 of the material dispenser 134 interact with portions of the housing 252 adjacent the bottom end 260 thereof. In other embodiments the slot 262 is provided in a sidewall or other portion of the housing 252. In the present embodiment the housing 252 is constructed from an injection-molded plastic, such as polypropylene. However, in other embodiments the housing 252 may be constructed from a different material such as glass or copolyester resin.

Figure 20:
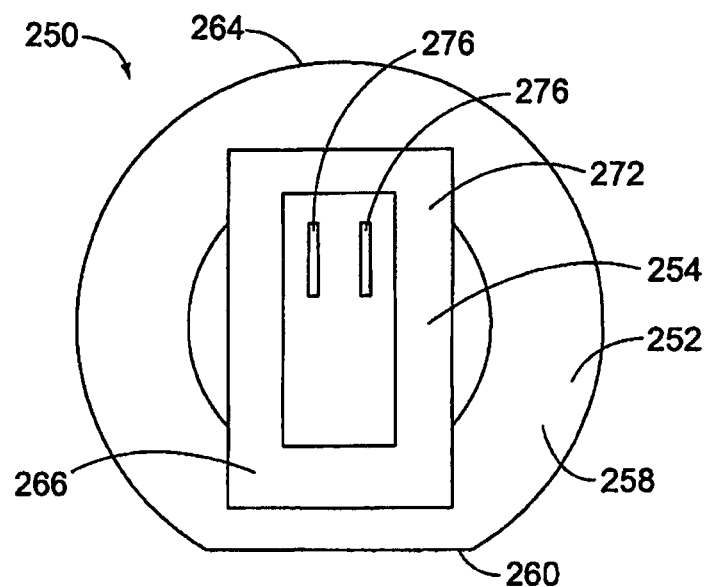
FIG. 20 is a rear elevational view of the volatile material dispensing system of FIG. 19 with the material dispenser removed.

Referring to FIG. 20, the electrical plate 254 is shown recessed within the back side 258 of the housing 252. The electrical plate 254 may be attached to the back side 258 by a snap fit, interference fit, adhesive, screws, or any other attachment means know to those of skill in the art. Alternatively, the electrical plate 254 may be integral with the housing 252. The electrical plate 254 includes a front surface 270 (see FIG. 19) and a rear surface 272 (see FIG. 20). The front surface 270 includes a heating element 274 substantially centrally disposed therein. The heating element 274 is similar to the ones described above and incorporated by reference herein, but may alternatively comprise any heating element known to those of skill in the art. Electrical prongs 276 are in communication with the heating element 274 and extend substantially perpendicularly from the rear surface 272 of the electrical plate 254. The electrical prongs 276 are adapted to be inserted into an outlet 278 (see FIG. 23) to provide power to the volatile material dispensing device 250.

Similar to other embodiments described herein, the volatile material dispensing system 250 is convertible from a passive or first operating state to an active or second operating state.

Following removal of the impermeable laminate 150, the volatile material dispensing system 250 begins to transition toward the empty or second condition and the volatile material 136 is dispersed into the atmosphere. The volatile material dispensing system 250 may be placed on a support surface (not shown) during the first operating state or may be electrically connected to an outlet 278 (see FIG. 23) with an activation switch, sensor, or other activation means (not shown) turned to an off position to allow for passive diffusion of the volatile material 136.

As illustrated in FIG. 23, the volatile material dispensing system 250 may be placed in an active or second operating state by inserting same into the outlet 278 or by activating the volatile material dispensing system 250 if it is already inserted into the outlet 278 by any of the activation means noted above. Upon activation, electrical power is supplied to the heating element 274 and heat is conducted through the electrical plate 254 to the material dispenser 134 in a similar manner as noted above. The heat supplied to the material dispenser 134 increases the rate of diffusion of the volatile material 136 and allows for the volatile material 136 to diffuse over a greater area or to provide for increased concentration of the volatile material 136 in a given area.

Figure 24:
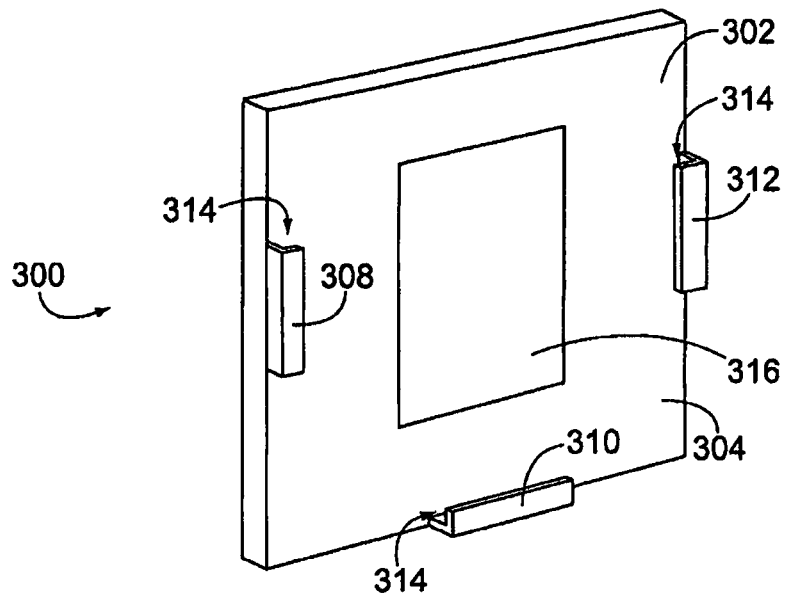
FIG. 24 is a front isometric view of yet another embodiment of a volatile material dispensing system that includes a base plate.
Figure 25:
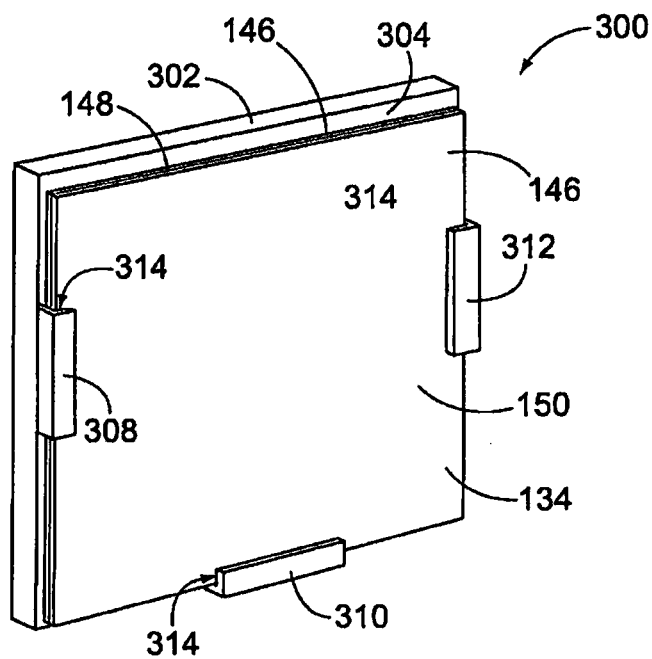
FIG. 25 is a view similar to the one shown in FIG. 24 except that a material dispenser is included within the base plate.
Figure 26:
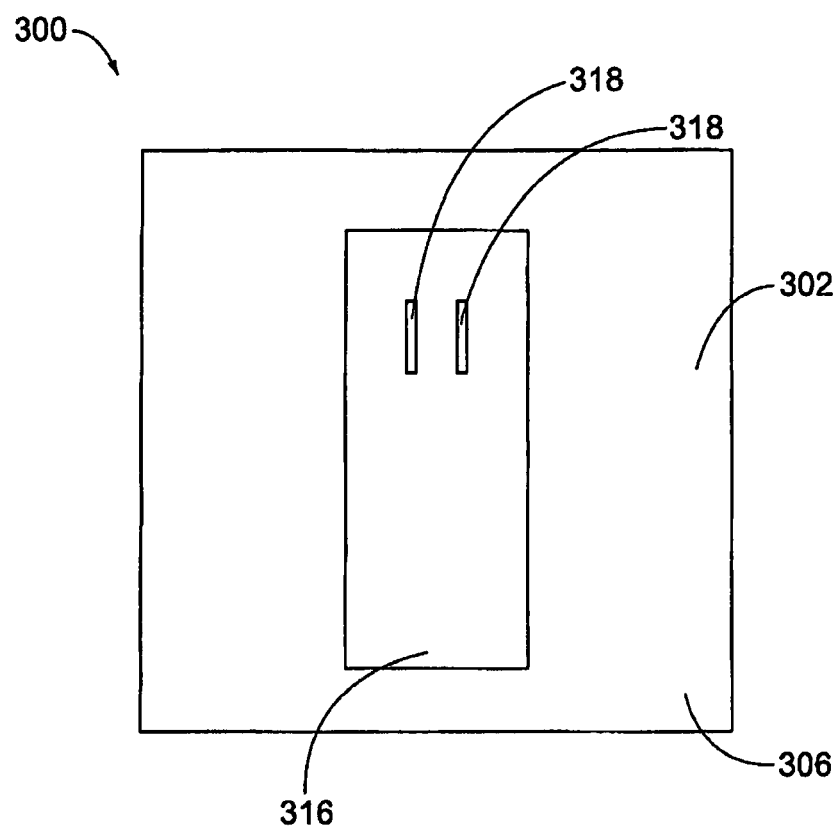
FIG. 26 is a rear elevational view of the volatile material dispensing system shown in FIG. 24.
Figure 27:
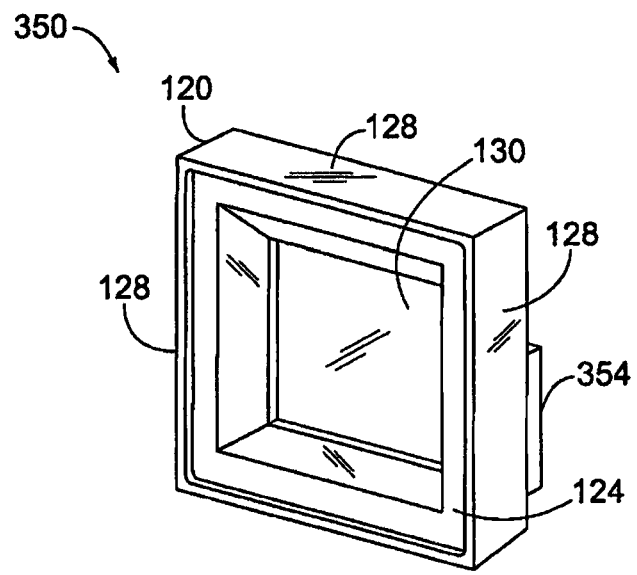
FIG. 27 is a front isometric view of a different embodiment of a volatile material dispensing system that includes a frame and a support member.
Figure 28:
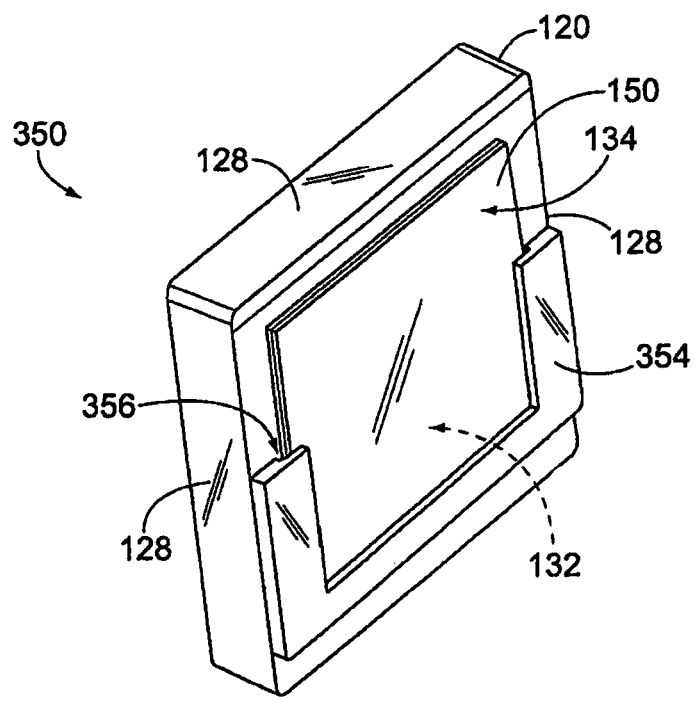
FIG. 28 is a rear isometric view of the volatile material dispensing system of FIG. 27 further including a material dispenser.
Figure 29:
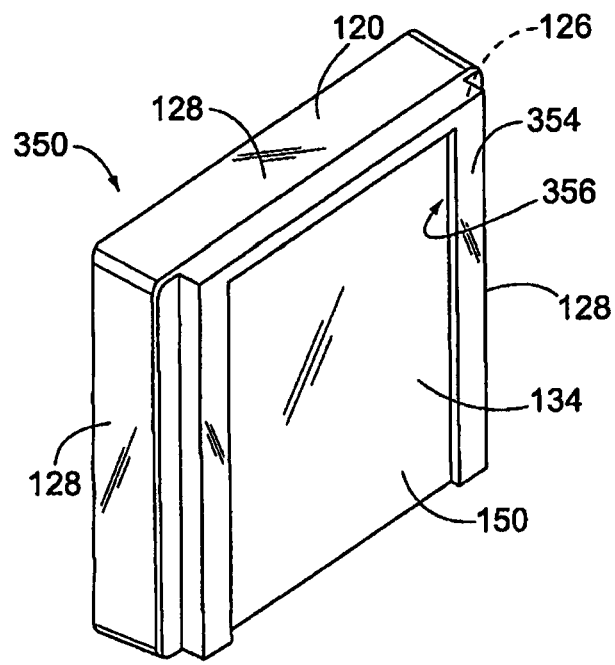
FIG. 29 is a view similar to the one shown in FIG. 28 except that the support member extends about three sides of the frame.

FIGS. 24-26 depict still another embodiment of a volatile material dispensing system 300, which includes a base plate 302 having a front side 304 and a rear side 306. The front side 304 includes first, second, and third flanges 308, 310, 312, respectively, spaced about a peripheral edge of the front side 304. The first, second, and third flanges 308-312 include notches 314 disposed therein. The surrounding flange 146 of the material dispenser 134, which has been described in connection with the other embodiments above (like reference numerals are used for identical structure), is adapted to be retained within the notches 314. The material dispenser 134 is placed on the front side 304 by sliding the surrounding flange 146 through the notches 314 on the first and third flanges 308, 312 and thereafter through the notch 314 in the second flange 310 to fully secure the material dispenser 314 on the base plate 302. When the material dispenser 134 is fully secured on the base plate 302, the bottom wall 142 of the cup-shaped structure 140 is held against the front side 304 of the base plate 302. Other securement mechanisms may include adhesive, other interference fit mechanisms, or any other component that adequately secures the material dispenser 134 to the base plate 302. Although three flanges are illustrated in the present embodiment, any number of flanges may be provided in alternative embodiments.

FIG. 24 depicts the front side 304 of the base plate 302, which includes a heating element 316 disposed centrally within the front side 304. The heating element 316 is adapted to conduct thermal energy through the material dispenser 134 in a second operating state to increase volatile material diffusion as described in connection with the other embodiments herein. Electrical prongs 318 for insertion into an outlet (not shown) extend substantially perpendicularly from the rear side 306 of the base plate 302 (see FIG. 26). The electrical prongs 318 are in electrical communication with a circuit (not shown) and the heating element 316. Similar to the other embodiments described herein, the volatile material dispensing system 300 may be operated in either a passive or active state dependent on whether the electrical prongs 318 are inserted into an outlet and/or whether any of the activation means described herein place the volatile material dispensing system 300 into an active state.

FIGS. 27-33 depict a different embodiment of a volatile material dispensing system 350, which includes a removable plate 352, a support member 354, and the frame 120 and the material dispenser 134, which are described in connection with the other embodiments above (like reference numerals are used for identical structure). The support member 354 is preferably U-shaped and is complementary to a width of the frame 120, i.e., extends the length of one of the sidewalls 128 and extends a portion of two of the other sidewalls 128 (see FIGS. 27 and 28). In a different embodiment (see FIG. 29) the U-shaped support member 354 extends the length of three of the sidewalls 128. It is contemplated that the U-shaped support member 354 may extend to a greater or lesser extent about one or more of the sidewalls 128 insofar as a channel 356 is provided for insertion of the material dispenser 134. The presently described U-shaped support members 354 are similar to those described in U.S. Pat. No. 7,426,799, which is incorporated herein by reference in its entirety. It is contemplated that the U-shaped members described in the U.S. Pat. No. 7,426,799 may be similarly used and/or modified to removably hold the material dispenser 134 and the removable plate 352 of the present embodiments.

Figure 30:
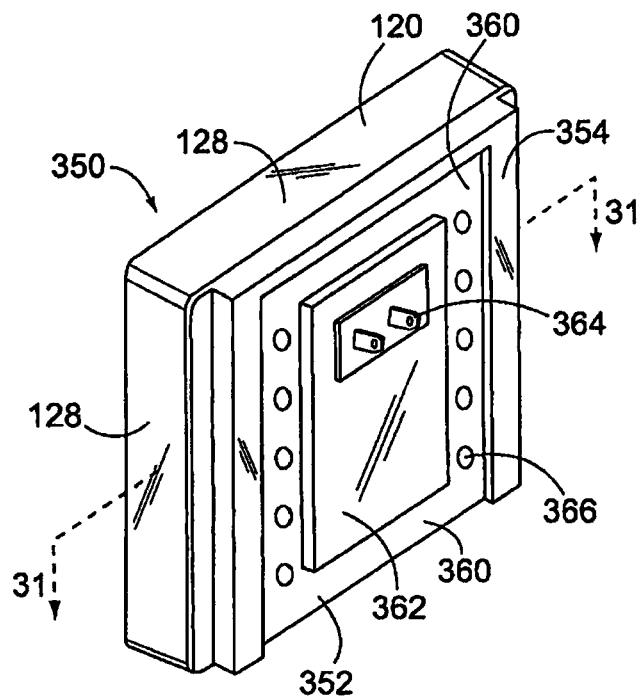
FIG. 30 is a view similar to the one shown in FIG. 29 except that a removable plate is disposed within the support frame.
Figure 31:
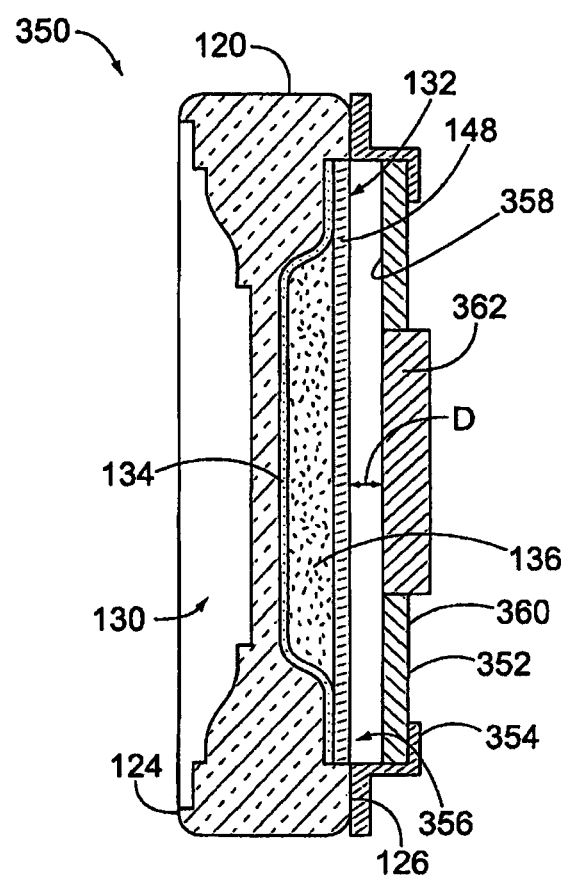
FIG. 31 is a sectional view taken generally along the line 31-31 of FIG. 30.
Figure 32:
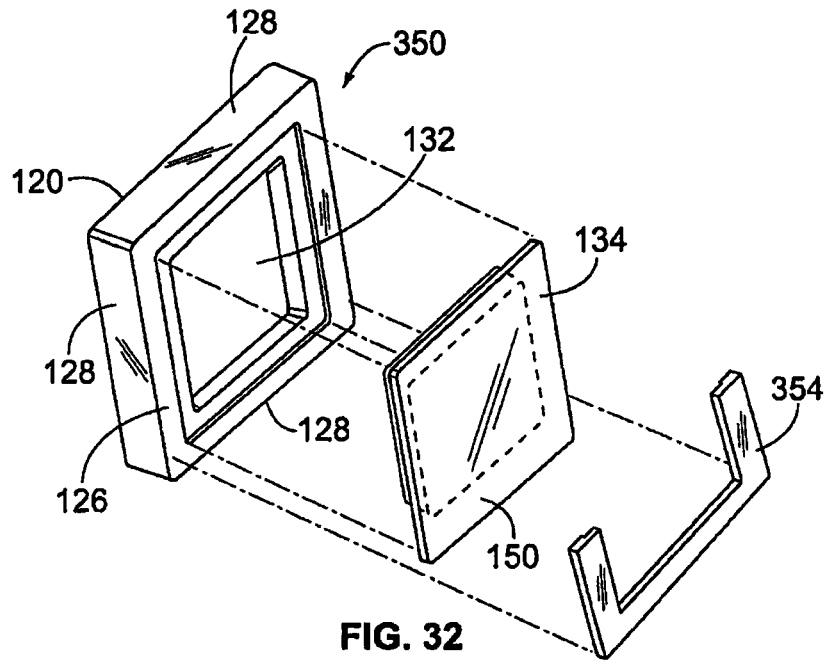
FIG. 32 is a rear exploded isometric view of the volatile material dispensing system shown in FIG. 27.
Figure 33:
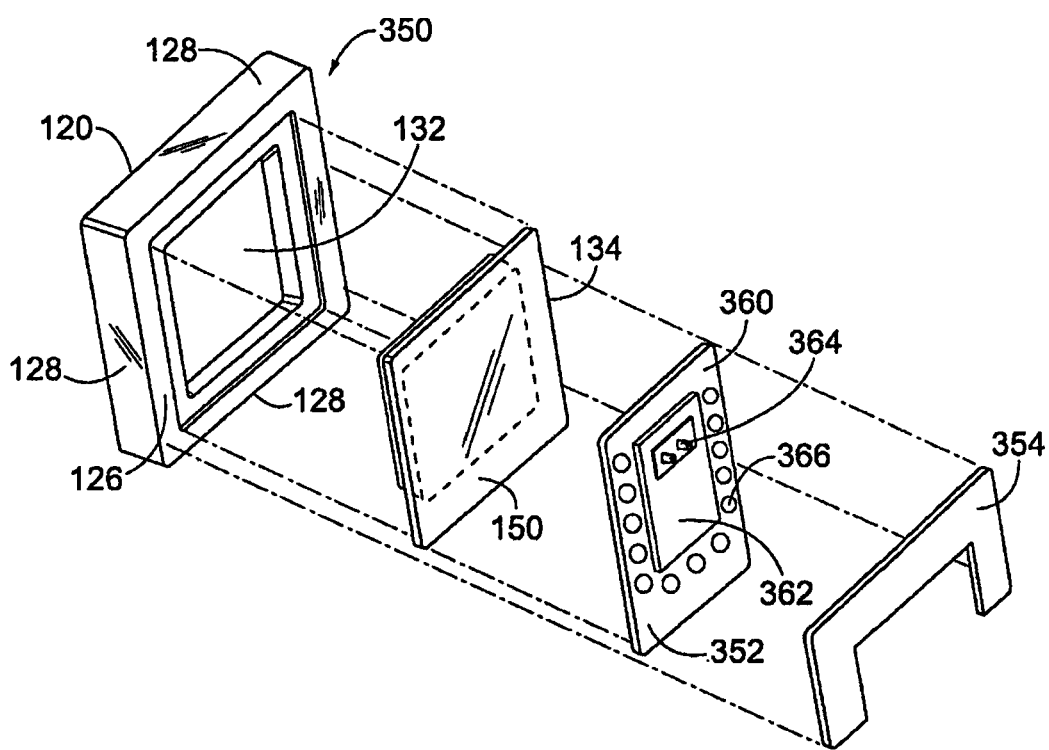
FIG. 33 is a view similar to the one shown in FIG. 32 except that a removable plate is shown.

As shown in FIGS. 30, 31, and 33, the removable plate 352 is generally square and includes a front side 358, a rear side 360, and a heating element 362. The heating element 362 extends through the front side 358 of the removable plate 352 and is in electrical communication with electrical prongs 364 extending substantially perpendicularly from the rear side 360 of the removable plate 352. The electrical prongs 364 are adapted to be inserted into an outlet (not shown) to provide power to the volatile material dispensing system 350. The removable plate 352 further includes at least one opening 366 to allow volatiles emanating from the material dispenser 134 to diffuse into the atmosphere. However, it is preferred that the removable plate 352 include a plurality of the openings 366 that surround the heating element 362. The removable plate 352 is preferably complementary to the shape and size of the frame 120 so that the removable plate 352 may be easily inserted into and removed from the channel 356 in the U-shaped support member 354.

The volatile material dispensing system 350 is similarly adapted to be converted between a passive or first operating state and an active or second operating state. For example, the impermeable laminate 150 of the material dispenser 134 depicted in FIGS. 28 and 29 may be removed and the material dispenser 134 inserted into the U-shaped support member 354. Thereafter, the material dispenser 134 is retained within the rear recess 132 of the frame 120 and is operating in a passive state to diffuse the volatile material 136. With reference to FIG. 30, the volatile material dispensing system 350 may be transitioned to the active state by inserting the removable plate 352 into the U-shaped support member 354 with the material dispenser 134 similarly disposed therein. The volatile material dispensing system 350 is thereafter positioned adjacent an outlet (not shown) so that the electrical prongs 364 may provide power to the heating element 362 and a circuit (not shown). The volatile material dispensing system 350 is either placed in an active state immediately upon inserting the electrical prongs 364 into the outlet (not shown) or in response to an activation means such as a switch, sensor, or any other activation mechanism contemplated herein (not shown). When the volatile material dispensing system 350 is placed in the active state, thermal energy from the heating element 362 heats the material dispenser 134 by convection to cause an increase in the volatilization of the volatile material 136 through the permeable membrane 148, wherein the volatiles are thereafter diffused into the atmosphere through the plurality of openings 366.

In the present embodiment it is preferred that a distance "D" (see FIG. 31) be maintained between the heating element 362 of the removable plate 352 and the permeable membrane 148 of the material dispenser 134. The distance "D" is preferably between about 1 mm and about 1 cm. The distance "D" ensures that the heating element 362 does not contact and/or move too close to the permeable membrane 148 so that same does not melt and allow leakage of the volatile material 136 or heat the permeable membrane 148 above a desirable temperature. It is also contemplated that spacers may be provided on portions of the front side 358 of the removable plate 352 to assist in maintaining the distance "D".

It is contemplated that the removable plate 352 will fittingly engage with interior portions of the U-shaped support member 354 in a manner that will allow for the volatile material dispensing system 350 to be inserted into an outlet (not shown) as a functional unit, i.e., the removable plate 352 will not slip out of the channel 356 and cause the frame 120 to separate from the removable plate 352. In other embodiments, a latching mechanism is provided to prevent separation of the removable plate 352 from the frame 120. Further, the volatile material dispensing system 350 may be rotated, e.g., 180 degrees from the position shown in FIGS. 27 and 28, so that portions of the removable plate 352 securingly interact with the U-shaped support member 354 (see FIGS. 30 and 33) when the electrical prongs 364 are inserted into the outlet (not shown). It is also envisioned that the volatile material dispensing system 350 can be rotated 90 degrees from the positions shown in FIGS. 27 and 28 or any other degree sufficient to prevent the removable plate 352 from disengaging with the U-shaped support member 354.

Figure 34:
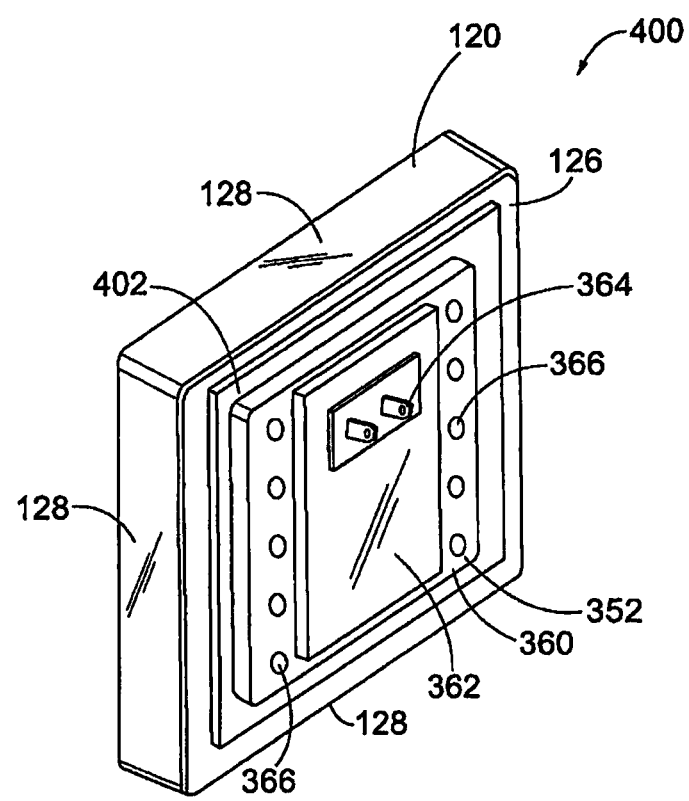
FIG. 34 is a rear isometric view of still another embodiment of a volatile material dispensing system.

FIG. 34 depicts a different embodiment of a volatile material dispensing system 400, which is identical to the previously described embodiment shown in FIGS. 27-33 except for the omission of the U-shaped support member 354 and the permanent attachment of the plate 352 to the rear face 126 of the frame 120. The plate 352 is attached to a spacing member 402. The spacing member 402 is secured to the rear face 126 of the frame 120 by screws (not shown). However, it is contemplated that the spacing member 402 may be secured to the frame 120 by any other securing means known to one of skill in the art. The spacing member 402 creates a space between the frame 120 and the plate 352 so that the material dispenser 134 may be inserted into the volatile material dispensing system 400 in a similar manner as noted above. The plate 352 similarly includes the openings 366 to allow volatiles to diffuse into the atmosphere.

The openings 366 of any of the embodiments described in FIGS. 27-34 may be circular or any other geometric shape and size. Further, one or more openings may be located in other positions on the removable plate 352, extend through the front face 124 of the frame 120, and/or the rear face 126 of the frame 120 in combination with the openings 366 or in lieu of same. For example, an opening (not shown) may be centrally disposed within the front recess 130 of the front face 124, which would allow the material dispenser 134 of any of the embodiments shown in FIGS. 27-34 to be rotated 180 degrees, i.e., the permeable membrane 148 would face away from the heating element 362, thereby reducing concerns of the permeable membrane 148 being exposed to undesirable temperatures.

Still further, the frame 120 and the removable plate 352 have been described in all of the previous embodiments as generally square in shape, but it is also contemplated that the frame 120 and the removable plate 352 may be shaped in other ways including, but not limited to, rectangular, oval, or other geometric shapes.

Figure 35:
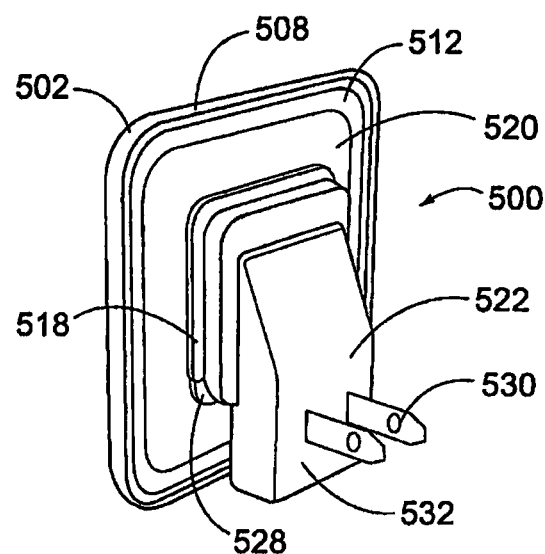
FIG. 35 is a rear isometric view of an embodiment of a modular volatile material dispensing system.
Figure 36:
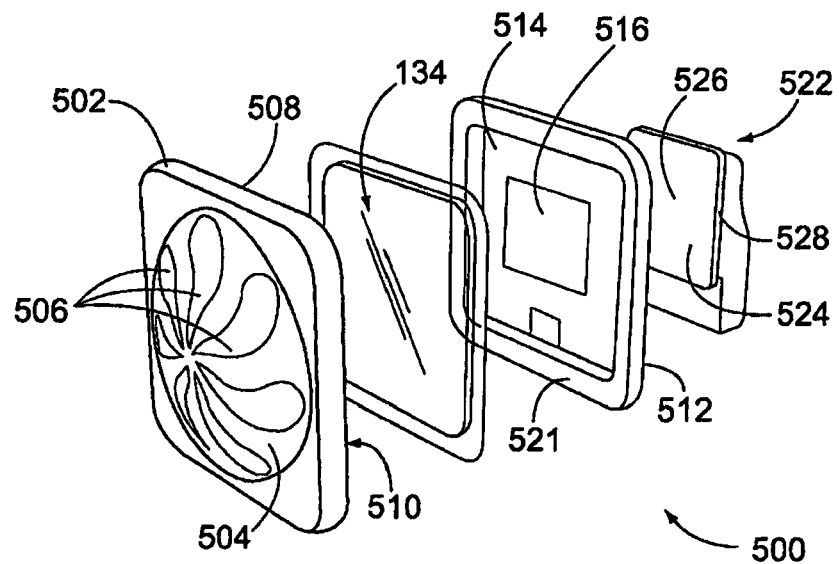
FIG. 36 is an exploded isometric view of the modular volatile material dispensing system of FIG. 35.

FIGS. 35 and 36 depict yet another embodiment of a modular volatile material dispensing system 500, which includes a generally square-shaped cover plate 502. The cover plate 502 includes a bulbous protrusion 504 having orifices 506 extending therethrough. A raised peripheral flange 508 extends around a rear side 510 of the cover plate 502. The supporting plate 512 is releasably attached to the cover plate 502 by an interference fit between peripheral portions of the supporting plate 512 and the raised peripheral flange 508 of the cover plate 502. In alternative embodiments, the cover plate 502 and the supporting plate 512 are attached by a snap fit connection, an adhesive, screws, or in any other manner known to one of skill in the art. The supporting plate 512 includes a centralized depression 514, which is substantially square-shaped. An opening 516 is provided in the supporting plate 512. A raised U-shaped protrusion 518 circumscribes a portion of the opening 516 on a rear side 520 of the supporting plate 512. A groove (not shown) is also provided between the rear side 520 and portions of the U-shaped protrusion 518.

Attachment of the cover plate 502 to the supporting plate 512 defines a compartment therebetween. Specifically, the compartment comprises the space between the rear side 510 of the cover plate 502 and a front side 521 of the supporting plate 512. During use, the volatile material dispenser 134 is positioned in the compartment so that the blister 138 of the volatile material dispenser 134 is seated within the centralized depression 514. Subsequently, the cover plate 502 is attached to the supporting plate 512 such that the compartment defined therebetween accommodates the volatile material dispenser 134.

The modular volatile material dispensing system 500 further includes a removable adapter, for example, an electrical plate 522. A front surface 524 of the electrical plate 522 includes a heating element 526 centrally disposed therein and a flange 528 extending about the periphery of the front surface 524. The electrical plate 522 is attached to the supporting plate 512 such that the heating element 526 extends through, or is adjacent to, the opening 516 to allow the heating element 526 to contact the bottom wall 142, or be otherwise adjacent to the bottom wall 142, of the volatile material dispenser 134 when the modular volatile material dispensing system 500 is assembled. In one embodiment, the electrical plate 522 is attached to the supporting plate 512 by sliding the flange 528 into the groove of the U-shaped protrusion 518 to create an interference fit therebetween. Electrical prongs 530 extend substantially perpendicularly from a rear surface 532 of the electrical plate 522 and are in electrical communication with the heating element 526.

The modular design of the volatile material dispensing system 500 allows a user to interchangeably mix and match cover plates with supporting plates, for example, to match the decor of a room or create a look that matches the scent being dispensed. In addition, the modular design allows the electrical plate 522 to be removed and replaced with a different modular adapter (see FIGS. 37-41). The modular adapters include a flange similar to the flange 528 on the electrical plate 522, which allows the modular adapter to be similarly inserted into the U-shaped protrusion 518 of the supporting plate 512. Alternatively, the modular adapter may be manufactured such that the edges thereof are sized to slide into the U-shaped protrusion 518 directly.

Figure 37:
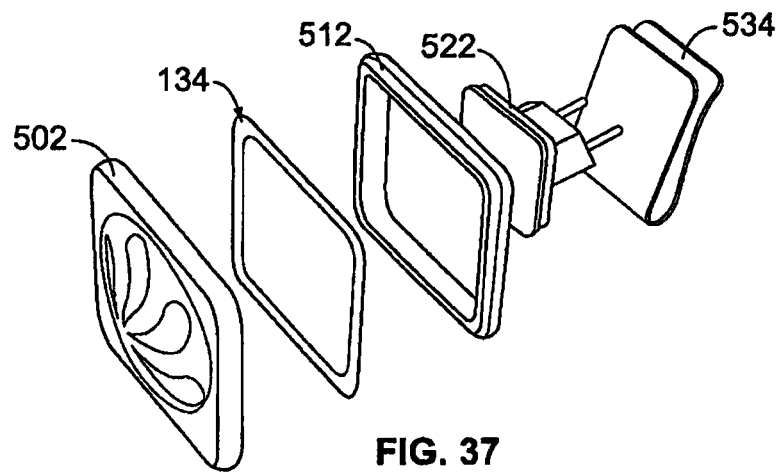
FIGS. 37-41 are exploded isometric views of further embodiments of a modular volatile material dispensing system.
Figure 38:
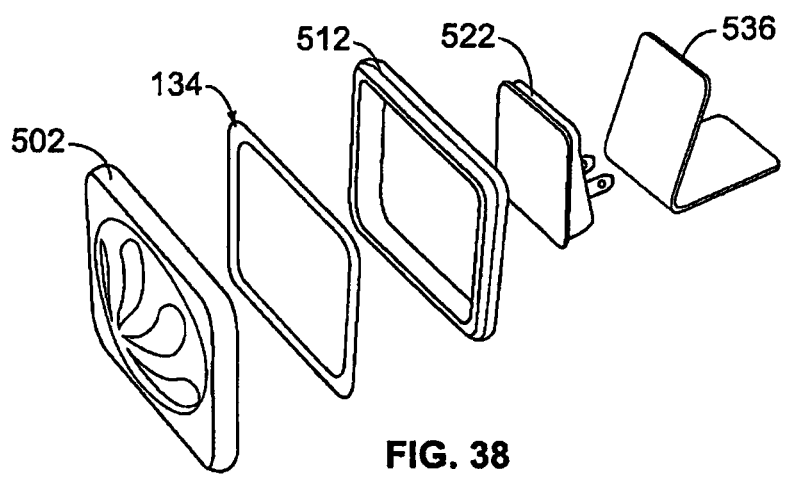
Figure 39:
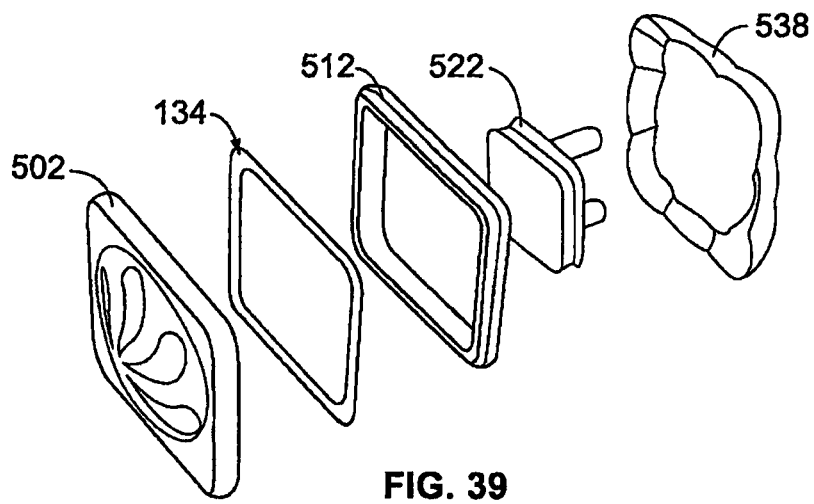

For example, as shown in FIG. 37, one such modular adapter comprises a substantially U-shaped clip 534 that is adapted to attach the modular volatile material dispensing system 500 to a surface, e.g., a car sun visor or a table edge. In another example, as shown in FIG. 38, the modular adapter includes a substantially L-shaped support 536 that allows the modular volatile material dispensing system 500 to remain in a substantially upright position when placed on a surface. In a further example, as shown in FIG. 39, a decorative housing 538, which provides a desirable ornamental appearance may attach to the supporting plate 512 over the electrical plate 522 or may be attached as a modular adapter in lieu of the electrical plate 522. Further, the decorative housing 538 may have a centralized hole (not shown) that allows for the electrical prongs 530 of the electrical plate 522 to extend therethrough. In another embodiment (not shown), the electrical prongs 530 of the electrical plate 522 may be folded flat against the electrical plate 522.

Figure 40:
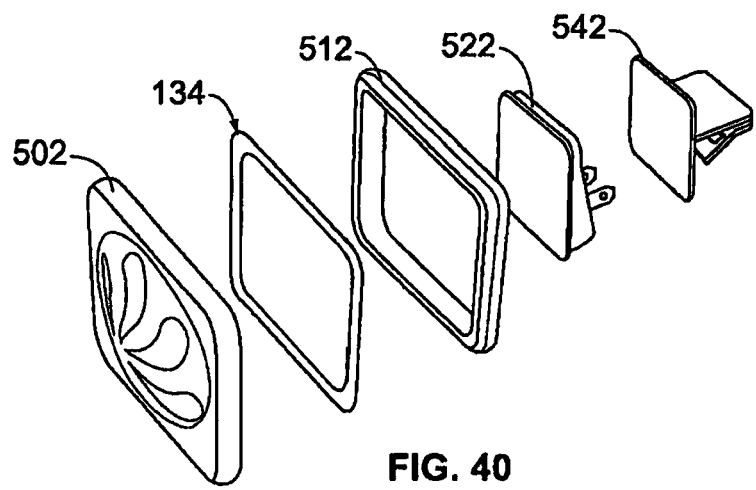

Another example of a modular adapter, as shown in FIG. 40, is an alligator clip adapter 540 that may be used to attach the modular volatile material dispensing system 500 to any type of protuberance. The alligator clip adapter 540 illustrated in FIG. 40 includes a top jaw that is fixed and a bottom jaw that is spring loaded to be held closed against the top jaw. Further, the jaws may be constructed to rotate in the plane of a base of the alligator clip adapter 540 such that the cover plate 502 may be rotated into a desired orientation after attachment of the alligator clip adapter 540 to the protuberance.

Figure 41:
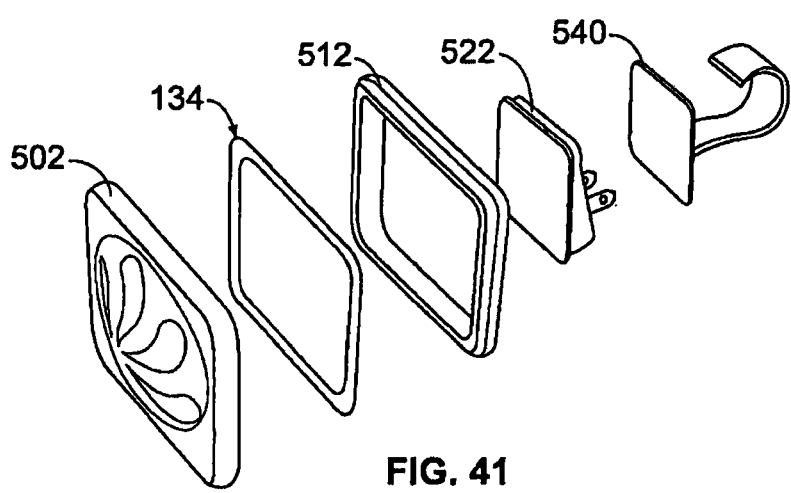

Another type of modular adapter, as shown in FIG. 41, is a hook adapter 542 that may be used to attach the modular volatile material dispensing system 500 to an attachment surface. For example, the modular volatile material dispensing system 500 could be hung from a nail or an overhang or attached to the louvers of a car air-conditioning vent. The hook adapter 542 may include a curved hook or a hook comprised of straight segments with corners therebetween such that the corners may provide a convenient catch against the attachment surface.

The modular design of the volatile material dispensing system 500 also offers practical benefits by allowing the modular parts to be manufactured separately to take advantage of potential cost savings and provide additional convenience in manufacturing. For example, each of the electrical plates 522 that are shown in FIGS. 37-39 have a different prong configuration. Prongs fitting electrical outlets in the United States could be manufactured at one site and prongs fitting another style of electrical outlet could be made at a different site. Further, product upgrades may be easier to implement in a modular design than in a one-piece design, because only a portion of the tooling may need to be changed in the implementation of an upgrade of a modular design.

Figure 42:
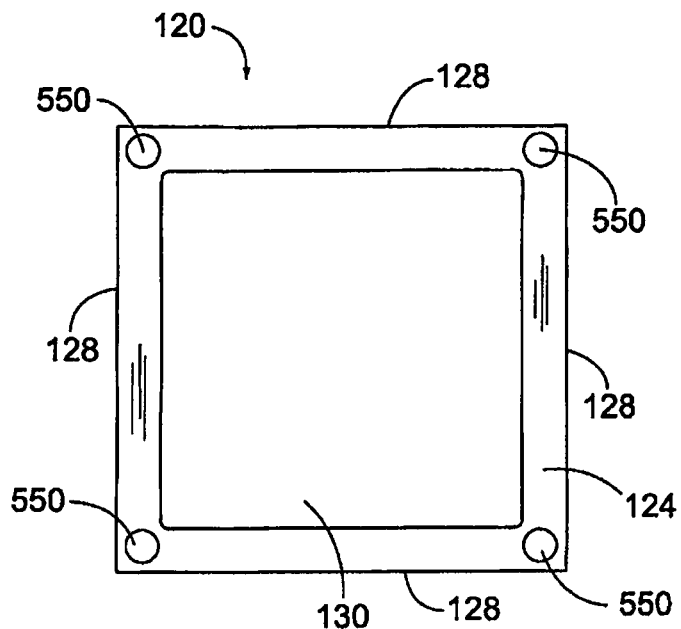
FIG. 42 is a front elevational view of an alternative embodiment of a dispensing device of any of the embodiments disclosed herein.

Turning now to FIG. 42, any of the frames 120, the cover plate 502, or the supporting plate 512 of the aforementioned embodiments may be modified to include one or more light sources 550. The light source 550 is preferably a LED or other similar lighting element that is embedded within the frame 120, the cover plate 502, or the supporting plate 512. In embodiments with the light source 550 embedded in the frame 120, the light source 550 is preferably connected to a circuit (not shown) located within a support base (not shown) using transparent wires (not shown). Alternatively, the wires may be one or more colors. In embodiments utilizing the cover plate 502 and the supporting plate 512, the light source 550 that is disposed therein may be connected to a circuit (not shown) located within the electrical plate 522 by contact surfaces that engage when the modular volatile material dispensing system 500 is assembled. Further, the light source 550 may be located on any portion of a base, a housing, and/or the frame 120. The light source 550 may be used in conjunction with other components such as a heating element or a sensor.

Figure 43:
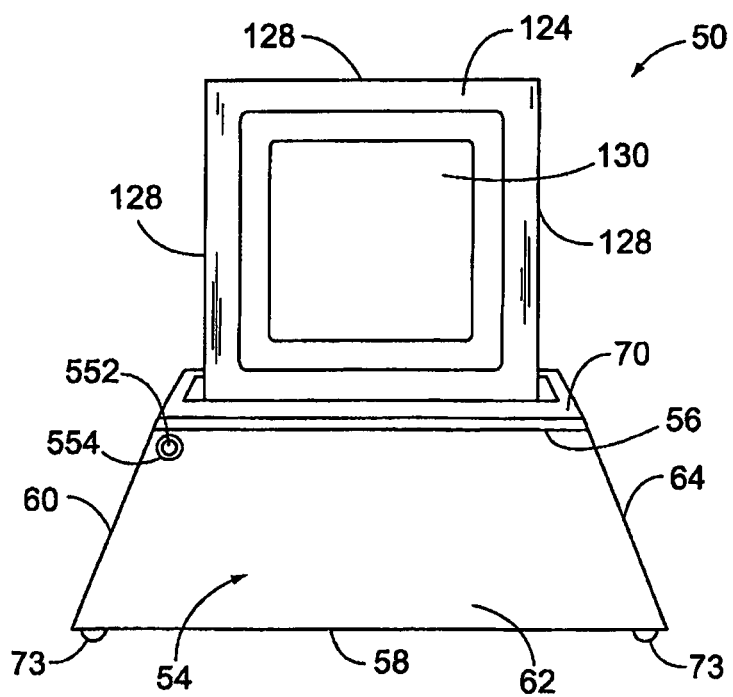
FIG. 43 is a front elevational view of a volatile material dispensing system similar to the one shown in FIG. 1 further including a sensor.

Now referring to FIG. 43, the volatile material dispensing system 50 is shown further including a sensor 552 provided within the support base 54. The sensor 552 is preferably located in an orifice 554 extending through one or more external surfaces of the top end 56 or the sidewalls 60-66 of the support base 54. Different types of sensors may be used independently or in combination including motion, light, and/or odor sensors. Other sensors may also be included as known to those of the skill in the art. The sensor 552 is preferably adapted to activate the heating element (not shown) and/or any of the previously described light sources in response to a sensed condition.

Any of the embodiments described herein may be modified to include any of the structures or methodologies disclosed in connection with different embodiments. Further, the present disclosure is not limited to volatile material dispensing systems of the type specifically shown. Still further, the frame or heating elements of any of the embodiments disclosed herein may be modified to work with any type of volatile material dispensing system.

INDUSTRIAL APPLICABILITY

A modular volatile material dispensing system is presented that dispenses volatiles in a passive state or an active state. A heating element is disposed in thermal contact with a volatile material dispenser to assist in diffusion of volatile material through a vapor permeable membrane of the volatile material dispenser in an active state. The modular volatile material dispensing system is adapted to interchange components to provide additional aesthetic and functional features.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A modular volatile material dispensing system, comprising:
    a supporting plate having a front side and a rear side and an opening extending therethrough, the rear side of the supporting plate being configured to removably attach to:
        an electrical plate including a heating element and electrical prongs, and
        a non-electrical plate including an adapter selected from the group consisting of a substantially U-shaped clip adapter having first and second arms, a substantially L-shaped support adapter, a hook adapter, and a clip adapter;
    a cover plate releasably attached to the front side of the supporting plate to form a compartment therebetween; and
    a volatile material dispenser adapted to be held within the compartment.

2. The modular volatile material dispensing system of claim 1, further including a decorative housing that attaches to the supporting plate.

3. The modular volatile material dispensing system of claim 1, further including a light source, which is in electrical communication with the electrical plate when attached to the supporting plate.

4. The modular volatile material dispensing system of claim 1, further including a sensor, wherein the sensor is configured to electrically connect to a circuit in the electrical plate and provide a control signal to energize at least one of a heating element and a light source when the electrical plate is attached to the supporting plate.

5. The modular volatile material dispensing system of claim 1, wherein the supporting plate includes a protrusion configured to removably attach to the electrical plate and the non-electrical plate.

6. The modular volatile material dispensing system of claim 5, wherein the protrusion is U-shaped.

* * * * *